United States Patent
Long

(10) Patent No.: US 6,576,465 B1
(45) Date of Patent: Jun. 10, 2003

(54) HUMAN BONE ACCESSORY CELLS

(75) Inventor: Michael W. Long, Northville, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/554,286

(22) PCT Filed: Nov. 10, 1998

(86) PCT No.: PCT/US98/23884

§ 371 (c)(1),
(2), (4) Date: Aug. 7, 2000

(87) PCT Pub. No.: WO99/24557

PCT Pub. Date: May 20, 1999

Related U.S. Application Data

(60) Provisional application No. 60/065,173, filed on Nov. 10, 1997.

(51) Int. Cl.[7] .............................. C12N 5/06; C12N 5/08
(52) U.S. Cl. ........................ 435/372; 435/366; 435/325
(58) Field of Search ............................... 435/372, 366, 435/325

(56) References Cited

U.S. PATENT DOCUMENTS

| | | | |
|---|---|---|---|
| 5,199,942 A | 4/1993 | Gillis | 604/4 |
| 5,340,925 A | * 8/1994 | Lioubin et al. | 530/395 |
| 5,409,825 A | 4/1995 | Hoffman et al. | 435/240.1 |
| 5,411,861 A | * 5/1995 | Seed et al. | 435/6 |
| 5,486,359 A | 1/1996 | Caplan et al. | 424/93.7 |
| 5,599,703 A | 2/1997 | Davis et al. | 435/373 |
| 5,605,822 A | 2/1997 | Emerson et al. | 435/172.3 |
| 5,646,043 A | 7/1997 | Emerson et al. | 435/37.3 |
| 5,658,761 A | 8/1997 | Thalmeier et al. | 435/69.4 |
| 5,840,502 A | * 11/1998 | Van Vlasselaer | 435/7.21 |
| 5,925,531 A | * 7/1999 | Pienta | 435/7.23 |
| 5,972,703 A | * 10/1999 | Long et al. | 435/372 |

FOREIGN PATENT DOCUMENTS

EP 0 798 374 10/1997

OTHER PUBLICATIONS

Long et al. Journal of Clinical Investigation. 1990. VOl. 86, pp. 1387–1395.*
Allen and Dexter, "The essential cells of the hemopoietic microenvironment," *Exp Hematol*, 12:517, 1984.
Canalis, "Effect of growth factors on bone cell replication and differentiation," *Clin. Orth. Rel. Res.*, 193:246–263, 1985.
Eipers et al., "Human bone marrow microenvironmental cells modulate bone precursos cell development," *Blood*, 8:631A, 1996.
Eipers et al., "Isolation and characterization of human bone marrow microenvironmental cells that regulate bone precursor cell proliferation," *Blood*, 90:402A, 1997.

Gronthos et al., "The STRO–1+ fraction of adult human bone marrow contains the osteogenic precursors", *Blood* 84:4164–4173, 1994.
Harigaya and Handa, "Generation of functional clonal cell lines from human bone marrow stroma", *Proc Natl Acad Sci USA*, 82:3477, 1985.
Long et al., "Expression of human bone–related proteins in the hematopoietic microenvironment," *J. Clin. Invest.*, 86:1387–1395, 1990.
Long et al., "Regulation of human bone marrow–derived osteoprogenitor cells by osteogenic growth factors," *J Clin. Invest* 95:881–887, 1995.
Muthukumaran and Reddi, "Bone matrix–induced local bone induction," *Clin. Orth. Rel. Res.*, 200:159–164, 1985.
Price et al., "Characterization of a gamma–carboxyglutamic acid–containing protein from bone," *Proc. Natl. Acad. Sci. USA*, 73:1447–1451, 1976.
Price et al., "Developmental appearance of the vitamin K–dependent protein of bone during calcification. Analysis of mineralizing tissues in human, calf, and rat," *J. Biol. Chem.*, 256:3781–3784, 1981.
Reddi, "Cell biology and biochemistry of endochondral bone development," *Coll. Res.*, 1:209–226, 1981.
Rickard et al., "Isolation and characterization of osteoblast precursor cells from human bone marrow", *J. Bone Miner. Res.* 11:312–324, 1996.
Robey et al., "Osteoblasts synthesize and respond to transforming growth factor–type beta (TGF–beta) in vitro," *J. Cell Biol.*, 105:457–463, 1987.
Shull et al., "Identification of a vitamin D responsive protein on the surface of human osteosarcoma cells," *Proc. Natl. Acad. Sci. USA*, 86:5405–5410, 1989.
Somerman et al., "Mechanism of fibroblast attachment to bone extracellular matrix: Role of 44kilodalton bone phosphoprotein," *J. Bone Min. Res.*, 2:259–265. 1987.
Stenner et al., "Monoclonal antibodies to native noncollagenous bone–specific proteins," *Proc. Natl. Acad. Sci. USA*, 81:2868–2872, 1984.
Termine et al., "Osteonectin, a bone–specific protein linking mineral to collagen," *Cell*, 26:99–105, 1981.
Urist et al., "Bone cell differentiation and growth factors," *Science*, 220:680–686, 1983.
Urist et al., Human bone morphogenetic protein (hBMP)[1] (41630), *Proceedings of the Society for Experimental Biology and Medicine*, 173:194–199, 1983.
Wozney et al., "Novel regulators of bone formation: molecular clones and activities," *Science*, 242:1528–1534, 1988.

* cited by examiner

Primary Examiner—Sandra E. Saucier
Assistant Examiner—Vera Afremova
(74) Attorney, Agent, or Firm—Fulbright & Jaworski L.L.P.

(57) ABSTRACT

Disclosed are compositions of bone accessory cells and methods for their preparation and use. Bone accessory cells are cells which are not hematopoietic and which can reconstitute the expression of bone proteins by human bone cells and support ex vivo expansion and/or differentiation of these cells. Such bone marrow-derived accessory cells are useful in the treatment of bone disorders and diseases, such as osteoporosis, or in promoting fracture repair. In addition, methods of diffenentiating bone precursor cells into osteoblasts, and other diagnostic and prognostic methods are provided.

27 Claims, 10 Drawing Sheets

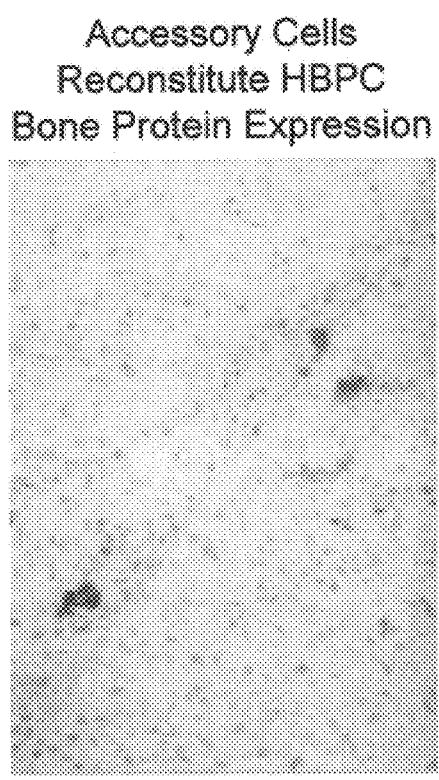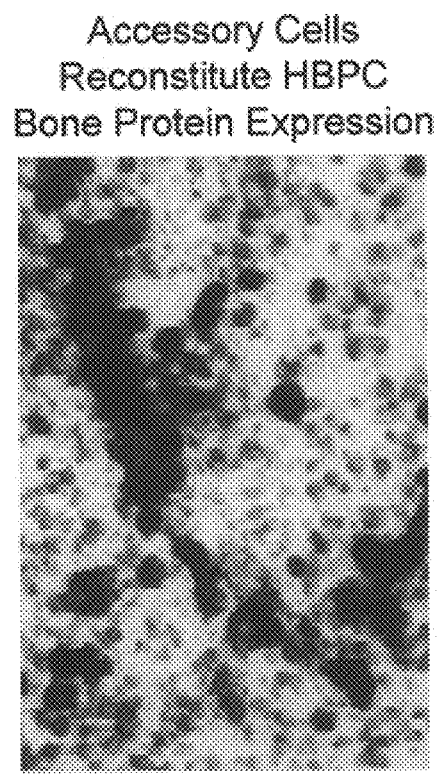
Accessory Cells Reconstitute HBPC Bone Protein Expression
HBPC + TGF-β
FIG. 1A
Accessory Cells Reconstitute HBPC Bone Protein Expression
HBPC + TGF-β + Accessory Cells
FIG. 1B Accessory Cells Are Not Typical Bone Marrow Stromal Cells Accessory Cells Are Not Typical Bone Marrow Stromal Cells Macrophage
(CD68)

NK Cells
(CD56)

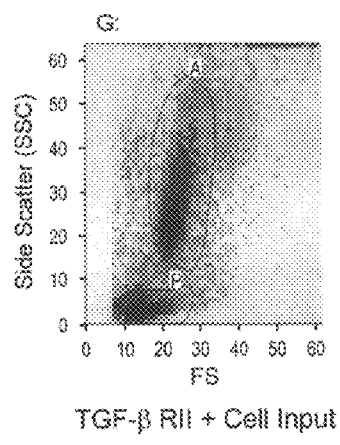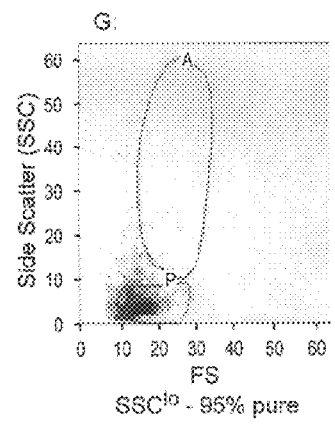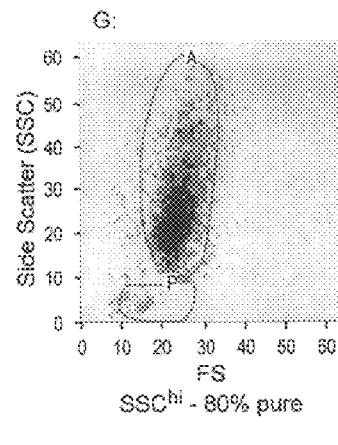
FIG.6A TGF-β RII + Cell Input
FIG.6B Post-Sort Analysis SSC$^{lo}$ - 95% pure
FIG.6C Post-Sort Analysis SSC$^{hi}$ - 80% pure

HUMAN BONE ACCESSORY CELLS

The present application is a continuation-in-part of U.S. Provisional Patent Application Ser. No. 60/065,173 filed Nov. 10, 1997. The entire text of the above-referenced disclosure is specifically incorporated by reference herein without disclaimer. The government owns rights in the present invention pursuant to grant number HL 59495 and AG 43460 from the National Institutes of Health.

BACKGROUND OF THE INVENTION

1. Field of the Invention

The present invention relates generally to the fields of bone cell development. In particular, it concerns the identification of a class of accessory cells that are useful in stimulating bone cells and their precursors.

2. Description of Related Art

The bone:bone marrow interface represents a relatively unexplored area of the bone marrow microenvironment in which both hematopoietic and osteopoietic cells exist in close opposition to each other. Such physical proximity suggests that these two cellular lineages interact (i.e., regulate) one another. However, little information exists concerning the intimate relationship between bone and bone marrow.

The precise role of accessory cells in bone formation is poorly understood. Accessory cells, however, are an important source of growth regulators required for the controlled differentiation and proliferation of progenitor cells in other systems (Kaushansky and Lin, 1988; Fibbe et al., 1988; Lee el al., 1987). In addition, these cells also provide complex, functional extracellular matrix components that stimulate bone cell development. Accessory cells are a heterogeneous cellular composition consisting of macrophages, fibroblasts, adipocytes, endothelial cells (Dexter, 1982; Allen and Dexter, 1984; Dexter et al., 1977), and other poorly defined cells. Such diversity makes it extremely difficult to analyze the role of each cell type in bone cell development.

Established accessory cell lines provide a useful tool for the analysis of discrete stromal functions. While a number of spontaneously immortalized murine cell lines have been described (Hunt et al., 1987; Quesenberry et al., 1987; Collins and Dorshkind, 1987) attempts to establish corresponding human lines have failed (Lanotte et al., 1981). Human bone marrow cell lines are also described in Thalmeier et al. (1992).

Some of the problems associated with the establishment of human stromal cell lines have been solved by introducing SV40 encoding DNA into the cellular genome (Harigaya and Handa, 1985; Novotny et al., 1990; Singer et al., 1987; Aizawa et al., 1991; Ciuttini et al., 1992). These stromal cell lines have been used as model systems for analyzing stromal cell-progenitor cell interactions (Yang et al., 1988; Kohama et al., 1988; Nemunaitis et al., 1989; Slack et al., 1990). Nevertheless, the use of SV40 immortalized stromal cell lines as supportive feeder layers in LTBMCs still has two important drawbacks. First, SV40-immortalized cells grow very rapidly (Neufeld et al., 1987) and then enter a characteristic crisis leading to the death of the cells (Singer et al., 1987). Second, SV40-immortalized stromal cells are readily detached from culture flasks upon inhibition by irradiation or mitomycin C (Ciuttini et al., 1992).

Further, understanding the complex regulatory signals required to coordinate cellular development necessitates an understanding of progenitor cell responses to cytokines, to the surrounding extracellular matrix molecules, and to cell:cell interactions (Long, 1992; Long et al., 1992). Pragmatically, this requires that investigations into the control of a given cellular lineage utilize purified precursor cell populations, serum-free culture conditions, and purified (e.g., recombinant) growth factors.

The isolation and purification of human bone precursor cells utilizing immunology-based technology also has been extensively studied (Long et al., 1995; Long et al., 1992). These bone precursor cells are characterized as small-sized cells that express low amounts of bone proteins (osteocalcin, osteonectin, and alkaline phosphatase) and have a low degree of internal complexity (i.e., are immature). When stimulated to differentiate, these preosteoblast-like cells become osteoblast-like in their appearance, size, antigenic expression, internal structure, and mineralize extracellular matrix (Long el al., 1995; Long et al., 1990).

Recently, another antigenic determinant, STRO-1, was identified as a marker of human osteogenic cells (Gronthos et al., 1994). STRO-1 identifies clonogenic bone marrow stromal progenitor cells (CFU-F) in adult bone marrow (Simmons and Torok-Storb, 1991). When placed in mineralizing conditions, a portion of STRO-1-positive CFU-F becomes alkaline phosphatase positive, responds to 1,25-dihydroxy vitamin $D_3$ (1,25-OH $D_3$) with increased osteocalcin production, and within four weeks undergoes mineralization (Gronthos et al., 1994). Thus, some STRO-1-positive bone marrow cells are clearly osteogenic in nature. Also, Riggs and colleagues have utilized negative immune selection to isolate a bipotential (i.e., osteoblast/adipocyte) precursor cell from human bone marrow (Rickard el al., 1996). All of the above investigations demonstrate that the use of partially purified bone cell populations allows the determination of phenotypic and functional data regarding the developmental characteristics of bone cells. Clearly, there are many studies that have attempted to isolate and purify populations of bone cells; however, to date, such studies have not addressed the necessity of microenvironmental accessory/stromal cells in regulating bone cell proliferation and/or differentiation.

Thus, there is a need to identify bone accessory cells that can proliferate at a high rate and can be used as accessory cells to support development of bone cells.

SUMMARY OF THE INVENTION

Therefore, the present invention provides compositions and methods relating to the stimulation of bone cells in vitro and in vivo.

The invention provides a method for isolating bone osteogenic accessory cells comprising the steps of (a) providing a starting cell population; (b) subjecting said population to density isolation to obtain a low density cell fraction; (c) subjecting said low density bone cell fraction to immune adherence based on TGFβII receptor expression; and (d) subjecting said immune adherent cells to positive selection based on cellular complexity. Also included in this method is plastic adherence and immunoaffinity purification. The immunoaffinity purification comprises selecting against osteonectin or osteocalcin expression or both. In addition, selection against expression of P-selectin, L-selectin, E-selectin, CD3, CD56, CD34, CD68 and vWF also is contemplated. The starting cell population may be any of a variety of cells but, in one embodiment, is bone marrow stromal cells.

Additional embodiments of the preceding method include culturing before or after any of steps (b)–(d), culturing said cells with an osteogenic cytokine, such as a member of the TGFβ super family of cytokines, e.g., TGFβ. The cells additionally may be characterized as between about 10 and about 70 μm in diameter.

In another embodiment, there is provided, a method of producing an osteogenic stimulatory factor comprising the steps of (a) culturing a cell population having the following characteristics: (i) having a buoyant density of between about 1.050 and about 1.090 g/cm³; (ii) absence of plastic adherence; (iii) presence of TGFβII receptor expression; (b) stimulating with TGFβ, and (c) collecting the culture medium. The cells further may be characterized as being low complexity ($SSC^{lo}$) cells.

In yet another embodiment, there is provided an isolated cell population having the following characteristics: (a) having a buoyant density of between about 1.050 and about 1.090 g/cm³; (b) absence of plastic adherence; and (c) presence of TGFβII receptor expression. The population also may be described as having the following characteristics: (a) presence of TGFβII receptor expression; (b) absence of expression of P-selectin, L-selectin, E-selectin, CD3, CD56, CD68, CD34 and vWF; and (c) low complexity as measured by flow cytometry.

In still yet another embodiment, there is provided a method for stimulating bone cell differentiation and/or maturation comprising the step of co-culturing a bone cell with an isolated cell population having the following characteristics: (a) having a buoyant density of between about 1.050 and about 1.090 g/cm³; (b) absence of plastic adherence; and (c) presence of TGFβII receptor expression. The bone cell, for example, may be an osteoprogenitor cell, a preosteoblast or an osteoblast. In various embodiments, the bone accessory cell is injected or is situated in an implantable device. Additionally, it is contemplated that the accessory cells further may be from a low complexity ($SSC^{lo}$) cell population, as measured by flow cytometry.

In a further embodiment, there is provided a method for stimulating bone cell differentiation and/or maturation comprising the step of culturing a bone cell with an osteopoeitic stimulatory factor produced by the step of culturing a cell population having the following characteristics: (a) having a buoyant density of between about 1.050 and 1.090 g/cm³; (b) absence of plastic adherence; and (c) presence of TGFβII receptor expression.

In still a further embodiment, there is provided a method for promoting the formation of bone comprising the steps of: (a) providing a bone cell; and (b) contacting said bone cell with a TGFβRII-positive bone accessory cell for a period of time sufficient to stimulate the development and/or growth said bone cell.

In still yet a further embodiment, there is provided a method for promoting the formation of bone comprising the steps of: (a) providing a bone cell; and (b) contacting said bone cell with a factor for a period of time sufficient to stimulate the development and/or growth said bone cell, wherein said factor is produced by a TGFβRII-positive bone accessory cell.

In yet other embodiments, there is provided a method for treating a subject having a bone disease comprising the step of providing to said patient a bone accessory cell, or a factor produced thereby. The bone disease may be, but is not limited to, osteoporosis, vitamin D deficiency, Von Recklinghausen's disease, osteitis deformans, osteomyelitis and fractures.

Also provided is a method for stimulating bone cell differentiation and/or maturation comprising the step of culturing a bone cell with a feeder layer of accessory cells having the following characteristics: (a) having a buoyant density of between about 1.050 and about 1.090 g/cm³; (b) absence of plastic adherence; and (c) presence of TGFβII receptor expression. In additional embodiments, the accessory cells may further be characterized as an $SSC^{lo}$ cell population.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A and FIG. 1B. Bone Accessory Cells Reconstitute the Expression of Bone Proteins by Human Bone Precursor Cells (HBPC). Highly purified HBPC, in the presence of TGFβ, fail to survive or proliferate over seven days of culture (FIG. 1A). Bone accessory cells permit survival and reconstitute proliferation and bone protein expression when admixed with HBPC (FIG. 1B). The immunocytochemical expression of osteocalcin is shown. In addition, reconstituted cells also express the bone-related proteins osteonectin and alkaline phosphatase.

FIG. 3B), Macrophages (CD68, FIG. 3C), and NK cells (CD56; FIG. 3D). FIG. 3A shows inappropriate Ab.

FIG. 5A shows the entire population of TFG-βRII⁺ cells isolated by immunological procedures. FIG. 5B demonstrates that the accessory cells characterized by the lowest extracellular complexity ($SSC^{lo}$) express the highest levels of TGFβRII.

FIG. 6A, FIG. 6B and FIG. 6C. Isolation of Subpopulations of TGFβRII-Positive Bone Accessory Cells by Fluorescence-Activated Flow Cytometry (FACS). FIG. 6A shows input cell populations, FIG. 6B shows a post-FACS analysis of purified $SSC^{lo}$ populations and FIG. 6C shows a post-FACS analysis of purified $SSC^{hi}$ populations.

DESCRIPTION OF ILLUSTRATIVE EMBODIMENTS

Figure 2:
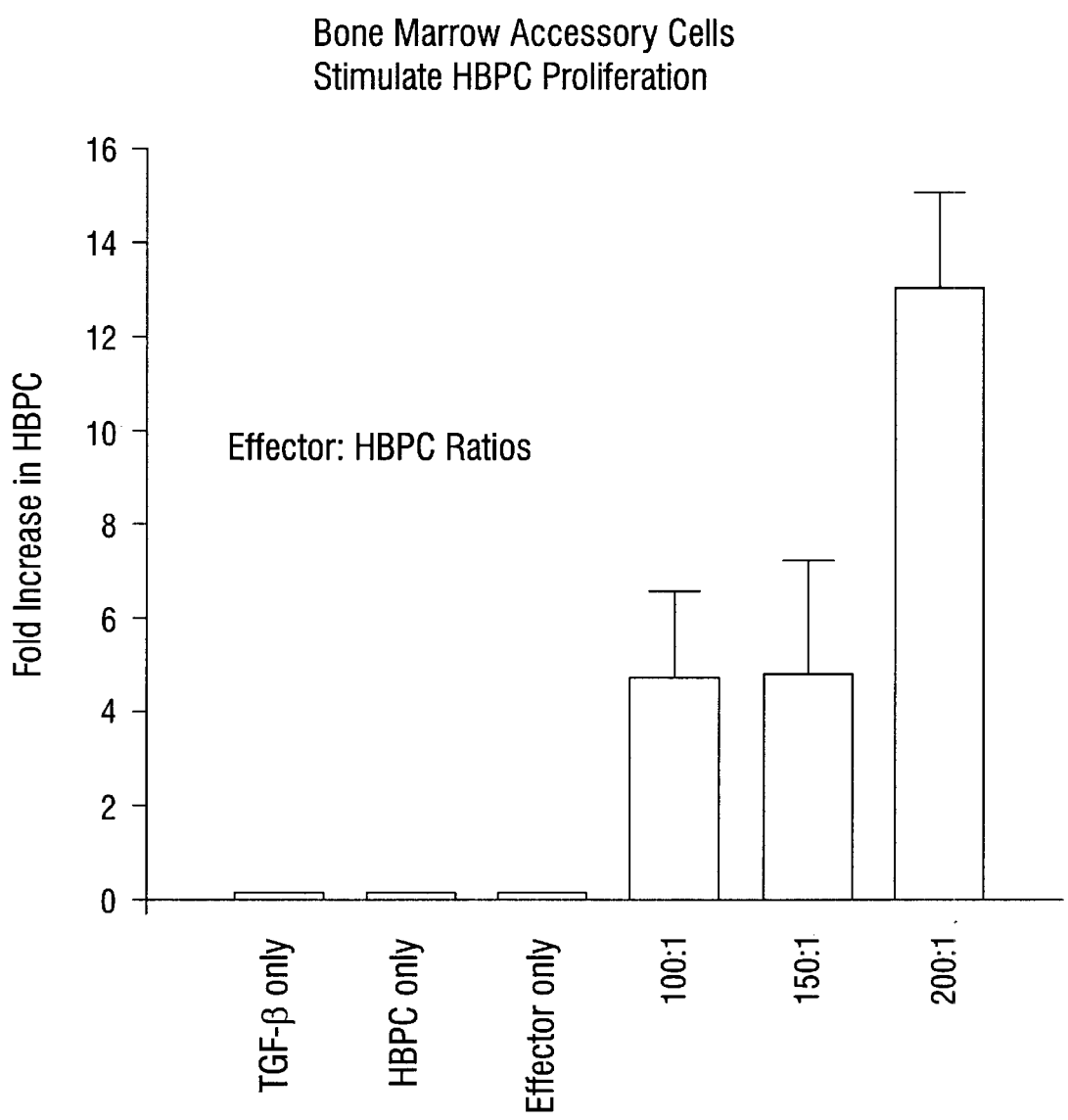
FIG. 2. Feeder Layers of Bone Accessory Cells Support the Ex Vivo Expansion of Human Bone Precursor Cells (HBPC). Feeder layers of crudely purified bone accessory cells (i.e., effector cells) stimulate up to about a 13±2—fold ex vivo expansion of HBPC (Target cells), at E to T ratios of about 100 to 200: 1, indicating that the bone accessory cells effect is mediated by a soluble growth factor produced by the accessory cells. Culture of bone marrow derived accessory cells in the absence of TGFβ fails to support HBPC, and culture of bone accessory cells only does not show osteogenic potential.

Previous work implies the existence of an accessory cell population that might be necessary for the outgrowth of bone precursor cells cells in vitro. Similar observations were made when immune-adherence technology was used in isolating cells. Subsequent to immune adherence, non-adherent cells are removed by three rounds of gentle washing. However, with increased "stringency" of the wash steps (by increasing either the shear-force, or the numbers of washes) the resultant immune adherent cells are positive for bone proteins such as osteocalcin or osteonectin, but these cells fail to develop in vitro. Also, it was noted that highly-purified populations of human bone precursor cells (i.e., those isolated by immunomagnetic separation) show the same flow cytometric characteristics and antigen expression as those cells isolated via immune-adherence, but essentially lack a contaminating population of cells which were antigenically negative. When these immunomagnetically purified human bone precursor cells (which are 100% viable) are cultured under the same conditions as cells isolated by immune adherence, they fail to grow in response to TGFβ. These observations led to the conclusion that human bone precursor cells might require an accessory cell population that is necessary for their growth. The present invention is directed to the identification of such an accessory cell population.

I. The Present Invention

Highly purified HBPC fail to develop, even in the presence of a cocktail of osteogenic cytokines. However, the present inventors have found that co-culture with crude populations of accessory cells reconstitutes both the proliferation of these cells and their expression of bone proteins. Through feeder layer studies, the inventors have elucidated the presence of a soluble factoror factors, that have osteogenic stimulatory activity (OSA) and do not require cell:cell interaction for activity.

Immune depletion studies show that T cells, macrophages, NK cells and endothelial cells do not produce the OSA observed by the feeder layers. Furthermore, the use of cytokines produced by the accessory cells failed to support HBPC development. In additional characterization studies, the inventors found that the soluble growth factor produced by the accessory cells cannot be replaced by EGF or VEGF, or their combination with TGFβ.

HBPC development does, however, have an absolute requirement for TGFβ1, thereby suggesting that the accessory cells respond to TGF β1. OSA producing effector cells isolated using antibodies against human TGFβ receptor type II yield an approximately 13-fold increase in the ex vivo expansion of HPBC. Upon further characterization using flow cytometry, the inventors identified a distinct cell population of relatively low cellular complexity (or maturity) of intermediate size, and of high TGFβRII expression. Cells sorted on these characteristics are enriched in bone accessory cells and show an increase in specific activity in HBPC expansion assays.

Previous reports have suggested that cells with osteogenic potential express the CFU-F antigen, STRO-1. However, flow cytometry of purified accessory cells shows that these cells express little, if any, STRO-1 antigen. The bone accessory cells of the present invention also lack expression of P-selectin, E-selectin or L-selectin. Additionally, it seems that these cells do not express, or express very little of the cell/matrix protein osteocalcin or osteonectin. The cells further lack expression of CD3 (a marker for T-cells), CD56 (an NK-cell marker), CD68 (a macrophage marker), CD34 (a hematopoietic cell marker), and von Willibrand's factor (an endothelial cell marker). Thus, these cells are not T-cells, hematopoietic cells, macrophages, NK-cells or endothelial cells. The cells are, however, characterized by high TGFβRII expression.

Figure 9:
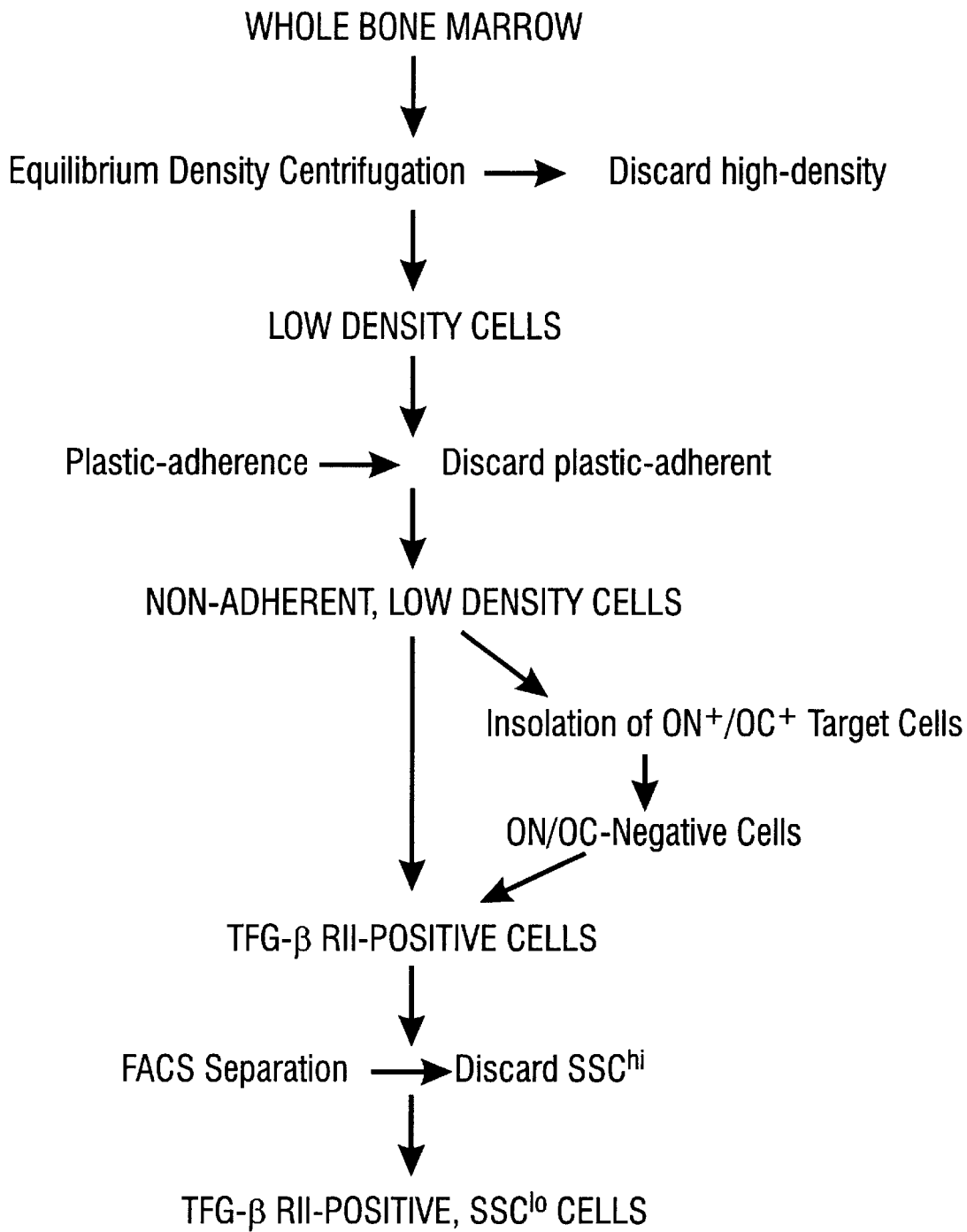
FIG. 9. Flow Diagram of the Isolation of Bone Accessory Cells.

In a preferred embodiment, the present invention provides methods of isolating OSA producing effector cells. FIG. 9 depicts a flow diagram of the isolation of the cells of the present invention from bone marrow although other osteogenic tissues can be used. A population of whole bone marrow cells are isolated using equilibrium density centrifugation, the low density fraction (LD; e.g., 1.066g g/cm²) is retained and the remaining density regions are discarded. LD cells are subjected to plastic-adhesion for 2–18 h (times>two h are immaterial to process, routine is 18 hrs/overnight). Common known stromal cells adhere to tissue culture plastic or glass, while bone precursor and accessory cells do not. The non-adherent (NA) cells population is collected. The resultant NALD cells also can be labeled with antibodies to osteonectin and osteocalcin (to remove target cells), and then labeled with antiimmunoglobulin antibodies conjugated to paramagnetic particles (commercially purchased). Labeled cells are exposed to a magnetic isolation column; the magnetic field retains human bone precursor cells, and allows the remainder of the NALD cells to elute. This eluted fraction forms the starting fraction for isolation of the bone marrow derived accessory cells (effector cells). The cells remaining in the magnetic field are human bone precursor cells (target cells).

An alternative embodiment provides a method for isolating the accessory cells without antibodies to osteonectin or osteocalcin. Bone accessory cells are separated from the NALD fraction by immune adherence to tissue culture dishes coated with antibody to TGFβ receptor type II (TGFβRII). TGFβRII-positive cells retain all the osteogenic stimulator activity, indicating their accessory cell phenotype. The TGFβ RII positive cells are removed from the immune adherent matrix, and used directly or further isolated using FACS. In this case, the bone accessory cells are separated based on their SSC characteristics. The purified $SSC^{lo}$ fraction of cells contain the TGFβRII positive, low complexity, large accessory bone marrow cells of the present invention. Accessory cells according to the invention are to be understood to mean also the active membrane-containing or subcellular fragments thereof which, analogous to the complete cells, promote the proliferation and/or differentiation of bone cells.

Thus, this process yields an accessory cell population that possesses osteogenic stimulatory activity for supporting the growth and differentiation of bone cells. Flow cytometric evaluation of these various isolated populations further characterize these cells as to their immunological phenotype, in particular, the purified bone accessory cells may be further negative selected to eliminate cells which express CD3, CD56, CD68, CD34, and von Willibrand's factor, using specific antibodies for these antigens.

As used herein, a bone precursor cell is any cell that is capable of differentiating or expanding into a preosteoblast and/or an osteoblast, and thus the term bone precursor cells includes osteoprogenitor cells of both the colony forming cell type and the cluster forming cell type and/or preosteoblast cells. A bone accessory cell of the present invention does not express the pan-hematopoietic antigen CD34.

"Supporting the proliferation of cells" as used in the invention is understood to mean that the isolated cells according to the invention support the survival, proliferation, and also the differentiation/development of bone cells. In this, the accessory cells of the present invention are bound to a surface (preferably a culture flask), a 3-dimension array, or established as a feeder layer in an inert matrix to allow the elaboration of bone growth factor(s). The target bone cells are layered over and settle onto that feeder layer and are stimulated to grow and/or differentiate. The feeder layer supplies the bone cells with OSA activity which may further be supplemented with other growth factors such as cytokines, and adhesion molecules. Another embodiment provides a method in which bone cells and accessory cells are cocultured, in varying ratios, in the absence of the inert matrix.

The term osteopoiesis (osteopoietic) is used herein to refer to the bone cell developmental process leading from the osteoprogenitor cell→preosteoblast→osteoblast. The term osteogenesis (osteogenic) refers to the generation of mineralized matrix/bone by maturing osteoblasts. The term osteopoiesis accessory cell (OAC) is used to refer to the accessory cell population of the present invention. The term OAC is synomous and used interchangeably with the term bone accessory cell throughout the present invention. These accessory cells are characterized by a $TGFβRII^+/SSC^{lo}$ phenotype and they possess osteogenic stimulatory activity (OSA).

In a preferred embodiment of the invention, the bone accessory cells according to the invention can be used for supporting the expansion of osteogenic precursor cells. The conditions for such expansion are described in a number of U.S. patents including U.S. Pat. No. 5,658,761; U.S. Pat. No. 5,646,043; U.S. Pat. No. 5,605,822; U.S. Pat. No. 5,599,703; U.S. Pat. No. 5,486,359; U.S. Pat. No. 5,409,825; U.S. Pat. No. 5199942; each of which is incorporated herein by reference. The methods described therein may be used for the expansion of osteogenic progenitor cells and may be supplemented with the accessory cells of the present invention to promote the growth of the HBPC.

In certain embodiments, it may be necessary to expand bone cells or their precursors without differentiation. Such an expansion may prove useful for the ex vivo proliferation of these cells following genetic modification. Such modified cells can be used in gene therapy. The transduction can be performed according to the state of the art, e.g., by using adenoviruses, retroviruses, DNA-calcium phosphate precipitation, direct gene insertion using a "gene-gun" or microinjection, electroporation or liposomes. As the yield of such a protocol usually is very low, and expanded modified cells are of great value in ex vivo gene therapy.

Another embodiment is the use of these bone accessory cells for ex vivo expansion of HBPC or osteoblasts for their use in a heterologous or allogeneic cell therapy, for example, in autologous bone marrow transplant.

The accessory cells, according to the present invention, can be used for all studies in which cells growing in dependency of a feeder layer are to be cultured. These cells include all precursor cells of bone formation and osteoblasts. Apart from being suitable feeder cells, the cells according to the invention, can be used as producer cells for an as yet unidentified but essential growth factor(s), necessary for the development of bone cells. Cell lines may be produced from these cells by immortalization.

Thus, the inventors have found that a unique accessory cell population that is required for the development of human osteogenic cells and that produces a soluble osteogenic stimulating activity. Presented herein are details for methods and compositions for the isolation and use of such cells and the growth factor repertoire they produce.

II. Bone Development and Growth Factors Thereof

Bone development results from the proliferation of mesenchymal cells, their differentiation into osteogenic progenitor cells, and the eventual calcification of cartilage or bone extracellular matrix (Urist et al., 1983). Human bone marrow contains a distinct cell population that expresses bone proteins and responds to growth factor β1 (TGFβ), but not to hematopoietic growth factors (Long et al., 1990).

Little information exists concerning the growth factors or cytokines controlling development of bone precursor cells (osteoprogenitor cells and preosteoblasts) into their differentiated progeny, the osteoblasts. Likewise, few studies address the impact of extracellular matrix (ECM) molecules on this stage of human bone cell development. In the past, human bone cells (both precursor cells and osteoblasts) have been technically difficult to acquire, and purification/characterization studies or protocols were few in number. Additionally, in vitro models of bone formation are limited as the use of post-fetal mesenchymal tissue to generate bone cells often results in chondrogenesis, but is inadequate for osteogenesis (Urist et al., 1983). Thus, information concerning the cellular activation signals, differentiation, and bone matrix production during the early phases of human bone cell development is limited at best.

The regulation of chondro-osteogenic gene activation is induced during bone morphogenesis by an accumulation of extracellular and intracellular signals (Urist el al., 1983). Importantly, extracellular signals are known to be transferred from both cytokines and extracellular matrix molecules (Urist et al., 1983), to responding cell surface receptor(s) resulting in eventual bone formation. The formation of bone occurs by two mechanisms. Direct development of bone from mesenchymal cells (referred to as intramembranous ossification; as observed in skull formation) occurs when mesenchymal cells directly differentiate into bone tissue. The second type of bone formation (the endochondral bone formation of skeletal bone) occurs via an intervening cartilage model.

The development and growth of long bones thus results from the proliferation of mesenchymal cells, their differentiation into osteogenic progenitor cells and (then) osteoblasts, cartilage deposition, and eventual calcification of the cartilage and/or bone matrix. Concurrently, bone is remodeled to form a tubular bone space in which hematopoietic cell differentiation occurs.

Like other developing tissues, bone responds to bone-specific and other soluble growth factors. TGFβ is a member of a family of polypeptide growth regulators that affect cell growth and differentiation during developmental processes, such as embryogenesis and tissue repair (Sporn and Roberts, 1985). TGFβ strongly inhibits proliferation of normal and tumor-derived epithelial cells, blocks adipogenesis, myogenesis, and hematopoiesis (Sporn et al., 1985). However, in bone, TGFβ is a positive regulator.

TGFβ is localized in active centers of bone differentiation (cartilage canals and osteocytes) (Massague, 1987), and TGFβ is found in high quantity in bone, suggesting that bone contains the greatest total amount of TGFβ (Massague, 1987 and Gehron Robey et al., 1987). During bone formnation, TGFβ also promotes chondrogenesis (Massague, 1987)—an effect presumably related to its ability to stimulate the deposition of extracellular matrix (ECM) components (Ignotz and Massague, 1986). Besides stimulating cartilage formation, TGFβ is synthesized and secreted in bone cell cultures, and stimulates the growth of sub-confluent layers of fetal bovine bone cells, thus showing it to be an autocrine regulator of bone cell development (Spom et al., 1985).

In addition to TGFβ, other growth factors or cytokines are implicated in bone development. Urist and co-workers have been able to isolate various regulatory proteins that function in both in vivo and in vitro models (Urist et al., 1983). Bone morphogenic protein (BMP), originally an extract of demineralized human bone matrix, now has been cloned (Wozney et al., 1988), and when implanted in vivo results in a sequence of events leading to functional bone formation (Wozney et al., 1988 and Muthukumaran et al., 1985). The implanting of BMP is followed by mesenchymal cell migration to the area of the implant, differentiation into bone progenitor cells, deposition of new bone, and subsequent bone remodeling to allow the establishment of bone marrow (Muthukumaran et al., 1985).

A number of non-collagenous matrix proteins, isolated from demineralized bone, are involved in bone formation. Osteonectin is a 32 kD protein which, binding to calcium, hydroxyapatite and collagen, is believed to initiate nucleation during the mineral phase of bone deposition (Termine et al., 1981). In vivo analysis of osteonectin message reveals its presence in a variety of developing tissues (Nomura et al., 1988 and Holland et al., 1987). However, it is present in its highest levels in bones of the axial skeleton, skull, and the blood platelet (megakaryocyte) (Nomura et al., 1988).

Bone gla-protein (BGP, osteocalcin) is a vitamin K-dependent, 5700 Da calcium binding bone protein that is specific for bone and may regulate Ca++ deposition (Termine et al., 1981; Price et al., 1976; Price et al., 1981).

Other bone proteins seem to function as cytoadhesion molecules (Oldberg et al., 1986; Somerman et al., 1987), or have unresolved functions (Reddi, 1981).

While bone morphogenesis is ECM-dependent, bone ECM also contains a number of the more common mesenchymal growth factors such as PDGF, basic, and acidic fibroblast growth factor (Urist et al., 1983; Linkhart et al., 1986; Hauschka et al., 1986; Canalis et al., 1985). These activities are capable of stimulating the proliferation of mesenchymal target cells (BALB/c 3T3 fibroblasts, capillary endothelial cells, and rat fetal osteoblasts). As well, bone-specific proliferating activities such as the BMP exist in bone ECM.

While these general and specific growth factors undoubtedly play a role in bone formation, little is understood concerning the direct inductive/permissive capacity of bone-ECM or bone proteins themselves on human bone cells or their progenitors. Nor is the role of bone ECM in presenting growth factors understood—such "matricrine" (factor:ECM) interactions may be of fundamental importance in bone cell development but have not been well characterized. The present invention, for the first time, demonstrates that there is a distinct cellular population in human bone marrow that contains a unique accessory cell population that is required for human osteogenic cell development.

III. Separation Techniques

The bone accessory cells of the present invention may be separated by a variety of techniques. These techniques are well known to those of skill in the art and are presented as exemplary methods of isolating cells of a particular composition and are by no means an exhaustive treatise on separation techniques. There are multiple texts on analytical techniques, and the skilled person is referred to Wilson and Goulding, 1991, and Freifelder, 1982, for further details.

The animal bone accessory cells described herein are isolated from animal bone marrow or other osteogenic tissues. This forms the starting cell population for the methods described herein. Sources of such a starting population include the flat bones of the axial skeleton (skull, ribs, hips, sternum), as well as the humeri, radi, ulanea, tibulae, and fibulae. Additionally, these cells can be obtained from other non-marrow sources including, but not limited to, the periosteum, bone trabeculae, cancellous bone, or the endosteum. Alternatively, the starting population also may be a bone marrow aspirate, bone graft material, or vertebral bodies.

Certain of the separation techniques employ immunologically-based procedures. These are comprised of, but not limited to, immune adhesion, fluorescence-activated flow cytometry, immunological-based column chromatography, antibody-conjugated sepharose beads (or other inert beads), or other immunology based applications (e.g. immuno-magnetic separation). These procedures do not however, define the population of animal bone accessory cells, but rather lead to its isolation.

Other physical separation procedures may be applied prior or after the antigenic purification. These are comprised of, but not limited to, equilibrium density centrifugation, velocity sedimentation, or counter-flow centrifugal elutriation. As well, other antigenic markers may be used in a positive or negative aspect, further define these cells. These are comprised of, but not limited to, antigens of the animal major histocompatibility locus (particularly HLA-DRA), hematopoietic antigens (e.g., CD33, CD8, CD10, CD14, CD9, CD20), or other bone proteins.

Bone accessory cells can be enriched by equilibrium-density centrifugation of bone marrow cells. Equilibrium-density centrifugation of bone marrow cells provides low density cells somewhat enriched in bone accessory cells with a density of between about 1.050 and about 1.090 gm/cm$^3$. In a preferred embodiment, the density of bone precursor cells is between about 1.060 and about 1.085 gm/cm$^3$. In one embodiment, equilibrium-density centrifugation can be performed before the immunoaffinity step. In this embodiment, the antibody purification step is carried out on bone marrow cells with a density of between about 1.050 and about 1.090. In a second embodiment, equilibrium-density centrifugation can be performed after the antibody purification of cells. Alternatively, the equilibrium-density centrifugation purification step can be performed twice— once before the antibody purification, and once after the antibody purification step.

In another aspect, the population of bone precursor cells can be enriched by removing plastic-adherent present in bone marrow cells. Removal of these cells can be accomplished by exposing bone marrow cells to an adherent surface, typically tissue culture plastic or glass. The cells adhere to tissue culture plastic or glass while bone accessory cells do not. Adherent cells can be removed before or after the immune purification step. Preferably, stromal cells are removed prior to the immune purification step. The use of solid surfaces such as tissue culture plastic or glass is well known in the art. Tissue culture plastic and glass can be treated (e.g. silicone, nitrocellulose, nickel, etc.) to promote or inhibit cell adhesion. Treated and untreated surfaces are available commercially.

In another aspect, an enriched population of bone precursor cells further is fractionated according to size. In a preferred embodiment, size fractionation can be accomplished by fluorescence activated flow cytometry. Bone accessory cells of the present invention have average diameters of between about 10 microns and about 70 microns, more preferably between about 10 microns and 20 microns.

Fluorescence Activated Cell Sorting (FACS)

FACS permits the separation of sub-populations of cells on the basis of their light scatter properties as they pass through a laser beam. The forward light scatter (FALS) is related to cell size, and the right angle light scatter, also known as side scatter characteristic (SSC) to cell density, cellular content and nucleo-cytplasmic ratio, i.e. cell complexity. Since cells can be labeled with fluorescent-conjugated antibodies, they can further be characterized by antibody (fluorescence) intensity. In exemplary embodiments, the FACS machine can be set to collect TGFβRII$^+$ (bright fluorescence) and TGFβRII$^-$ (low fluorescence) cells.

In order to label marrow cells with an antibody, for example a TGFβRII monoclonal antibody, cells may be prepared as described in Example 1. The bone marrow cell preparation is divided into aliquots comprising about 1×10$^5$ to 1×10$^6$ per ml in a centrifuge tube. This suspension is then centrifuged in a bench topor other centriftige. The cell pellet thus generated is then resuspended in a suitable buffer, contains the monoclonal antibody of choice and allowed to incubate for an appropriate period of time. The labeled cells are washed and an aliquot of the labeled cells is incubated with fluorescein labeled anti-mouse immunoglobulins. This suspension is washed and resuspended in a suitable buffer for cell sorting.

In sorting cells by FACS, a window (i.e., an electronically defined region) for low SSC and intermediate size (FALS) is set. The cells in this window are further divisible by antibody-fluorescence activity. The FACS settings are calibrated to collect cells positive and negative for the particular antigen.

In particular embodiments, of the present invention the bone accessory cells were characterized by FACS. These cells had low cellular complexity defined by right angle light scatter and intermediate size, defined by high forward angle scatter.

Chromatography

As an alternative to FACS, cells may be isolated using immune-isolation. The availability of antibodies against TGFβRII allows for the specific separation of bone accessory cells, whereas the presence of other antigens such as CD34$^+$ allows for a variety of chromatography methods to be employed in the separation of such cell populations. In certain embodiments of the invention, it will be desirable to produce functional TGFβRII$^+$, CD34$^-$, CD3$^-$, CD56$^-$, CD68$^-$, von Willibrand's factor$^-$ (vWF$^-$), osteocalcin$^-$ and osteonectin$^-$ cells from the bone marrow. Purification techniques are well known to those of skill in the art. These techniques tend to involve the fractionation of the cellular milieu to separate the bone marrow cell fraction containing the desired cell from other components of the mixture using standard immunological procedures such as, but not limited to, immunomagnetics, immunoadhesion, and the like. Having separated bone marrow cell fraction as described above, the TGFβRII$^+$, CD34$^-$, CD3$^-$, CD56$^-$, CD68$^-$, von Willibrand's factor$^-$ (vWF$^-$), osteocalcin$^-$ and osteonectin$^-$ cells may be purified further using various separative to achieve further purification. Analytical methods particularly suited to the preparation of a pure cell surface antigens use chromatography.

Affinity chromatography is a chromatographic procedure that relies on the specific affinity between a substance to be isolated and a molecule that it can specifically bind to. This is a receptor-ligand type of interaction. The column material is synthesized by covalently coupling one of the binding partners (in this case the antibody) to an insoluble matrix. The column material is then able to specifically adsorb the substance from the solution. Elution occurs by changing the conditions to those in which binding will not occur (alter pH, ionic strength, temperature, etc.).

One of the most common forms of affinity chromatography is immunoaffinity chromatography. The generation of antibodies that would be suitable for use in accord with the present invention is discussed below. The antibody or antigen is attached to an insoluble, inert matrix. The cell population to be separated is applied to the matrix such that there is a specific antibody-antigen interaction. The bound antigen/antibody is eluted from the adsorbent by exposure to mildly denaturing solvents, such as low pH buffers, high salt concentrations and the like.

In particular embodiments, the bone marrow accessory cells of the present invention, are isolated using immnnuo-magnetic chromatography. For example, an anti-TGFβRII antibody is attached to magnetic beads. These antibody labeled magnetic beads are used as the basis for the affinity purification. The antobidy-labeled low density, non-adherent fraction of whole bone marrow cells are applied to the magnetic affinity column. The non-adherent cells are discarded and the adherent cells are eluted from the magnetic column by removal of the magnetic field. In another embodiment, the cells are first labeled with an antibody (e.g., anti-TBGβRII) and then labeled with a secondary antibody carrying a magnetic bead or sphere.

Another type of affinity chromatography useful in the purification of carbohydrate containing compounds is lectin affinity chromatography, this type of chromatography will be useful in removing CD34+ cells. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

Magnetic Immunoselection

Immunoselection using magnetic beads employs beads that are precoated with the desired monoclonal antibody. Cells may be precoated with monoclonal antibody and attached to the magnetic bead through a secondary anti-mouse immunoglobulin attached to the bead. The cells bound to the beads are then removed with a magnet. This is a rapid method that allows for a high yield of cells.

Immune Adhesion

In immune adhesion, plastic coated surfaces are employed to isolate cells from a mixture. A surface such as a petri dish is coated with an antibody that selects cells that possess a desired phenotype. Cells are placed onto the coated dish and incubated for a suitable period of time to allow for an interaction between the cells and the coating of the dish. After the incubation period non-adherent cells are removed by gentle washing with a suitable buffer. The antibody-adherent cells that remain attached to the dish may then be cultured and/or recovered using trypsinization or other cell harvesting techniques well known to those of skill in the art.

Bone accessory cells of the present invention are immunoreactive with TGFβRII antibody. Such an antibody is used to enrich the population of bone accessory cells. As the bone accessory cells are further characterized, other antibodies which immunoreact with a bone accessory cell may be generated by one of ordinary skill in the art. The use of these other antibodies immunoreactive with a bone accessory cell are contemplated as well.

In another embodiment, a second antibody immunoreactive with a bone accessory cell antibody can be used to enrich the population of bone accessory cells. The use of a secondary antibody is generally known in the art. Typically, secondary antibodies are antibodies immunoreactive with the constant regions of the first antibody. Preferred secondary antibodies include anti-rabbit, anti-mouse, anti-rat, anti-goat, and anti-horse immunoglobulins and are available commercially. In a preferred embodiment, secondary antibodies are conjugated to a solid substrate including tissue culture dish, agarose, polyacrylamide, and magnetic particles. In this embodiment, a bone accessory cell antibody is first immunoreacted to a bone accessory cell. The bone accessory cell with the attached antibody is next exposed to the secondary antibody that is conjugated to a solid substrate. Enrichment of cells is achieved because only cells that are labeled with a bone accessory cell antibody immunoreact with the secondary antibody. A commercially available kit provides secondary antibodies conjugated to magnetic particles. In this system, bone accessory cells that present a bone accessory cell antibody are purified by exposure to a magnetic field.

IV. Monoclonal Antibodies

Many of the techniques disclosed herein are immunologically-based procedure and employ antibodies. The preparation of bone protein antibodies was reported in Shull el al., 1989, incorporated herein by reference, similar methods may be used to generate antibodies against the bone accessory cells of the present invention. Both polyclonal and monoclonal antibodies are contemplated by the present invention. Means for preparing and characterizing antibodies are well known in the art (See, e.g., *Antibodies* "A LABORATORY MANUAL, E. Harlow and D. Lane, Cold Spring Harbor Laboratory, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster, a sheep or a guinea pig. Because of the ease of use and relatively large blood volume of rabbits, a rabbit is a preferred choice for production of polyclonal antibodies.

A monoclonal antibody can be readily prepared through use of well-known techniques such as those exemplified in U.S. Pat. No. 4,196,265, herein incorporated by reference.

Typically, a technique involves first immunizing a suitable animal with a selected antigen in a manner sufficient to provide an immune response. After a sufficient time to induce an immune response, spleen cells from the immunized animal are then fused with cells of an immortal myeloma cell. A number of immortal myeloma cells are available and the choice of the immortal cell is within the skill of an artisan. Immortal myeloma cells lack the salvage pathway of synthesizing nucleotides.

The fused spleen/myeloma cells are cultured in a selective medium to select fused spleen/myeloma cells from the parental cells. Fused cells are separated from the mixture of non-fused parental cells by the addition of agents that block the de novo synthesis of nucleotides in the tissue culture media. Unfused myeloma cells lack the enzymes necessary to synthesize nucleotides from the salvage pathway and are selectively killed in the selective media. Unfused lymphocytes also do not continue to grow in tissue culture. Thus, only cells that have successfully fused (hybridoma cells) can grow in the selection media. The hybridoma cell produces a monoclonal antibody.

In various embodiments of the present invention, monoclonal antibodies against various immunodeterminants of bone marrow cells are employed. These antibodies may be raised according to the methods described herein or are readily available from for example the American Tissue Culture Collection, (ATCC). One of skill in the art is referred to the ATCC catalogue, 7th edition pages 319-332 incorporated herein by reference, for list of such antibodies. Particularly useful antibodies include, but are not limited to CRL 8001 and HB 231 for CD3; CRL 8034, CRL 8035 for hematopoietic cells; HB 215 for hematopoietic stem cell antigen; HB 8491, HB 8489, HB 8488, HB 8662, HB 8486, HB 8487, HB 8485, HB 8437, HB 8490, and HB 155 for epithelial cells; HB 172, HB 174 and TIB 228 for human macrophages.

V. Complement Fixation

In certain embodiments, the cells of the present invention may be selected using negative selection for immunophenotypes such as CD34, CD3, CD56, CD68, von Willibrand's factor (vWF). In an exemplary embodiments, the negative selection may employ antibody-mediated complement-dependent cell killing. Complement is a collective term for a large number of proteins which form the effector mechanism of immunity (for reviews see Reid 1988; Morgan 1990). Complement reacts not with antigen or antibody alone but with a variety of antigen-antibody complexes.

VI. Implantable Devices

The present invention contemplates methods for co-culturing a bone cell with an isolated cell population in which the accessory cell (or even the bone cell) is situated in an implantable device. The present section provides a description of the types of implantable devices contemplated to be useful in the context of the present invention.

In some aspects, the cells may be encapsulated in a biocompatible coating. In this approach, the cells are entrapped in a capsular coating that protects the contents from immunological responses. One preferred encapsulation technique involves encapsulation with alginate-polylysine-alginate. Capsules made employing this technique generally have a diameter of approximately 0.5 to 1 mm and should contain several hundred cells.

Cells may thus be implanted using the alginate-polylysine encapsulation technique of O'Shea and Sun (1986), with modifications as later described by Fritschy et al. (1991; both references incorporated herein by reference). An alternative approach is to seed Amicon fibers with accessory cells of the present invention. The cells become enmeshed in the fibers, which are semipermeable, and are thus protected in a manner similar to the microencapsulates (Altman et al., 1986; incorporated herein by reference). After successful encapsulation, the cells are delivered to the site of choice.

A variety of other encapsulation technologies have been developed that are applicable to the practice of the present invention (see, e.g., Lacy et al., 1991; Sullivan et al., 1991; WO 91/10470; WO 91/10425; WO 90/15637; WO 90/02580; U.S. Pat. No. 5,011,472; U.S. Pat. No. 4,892,538; U.S. Pat. No. 5,002,661, U.S. Pat. No. 5,569,462, U.S. Pat. No. 5,593,440, U.S. Pat. No. 5,549,675, U.S. Pat. No. 5,545,223, U.S. Pat. No. 5,314,471, U.S. Pat. No. 5,626,561 and WO 89/01967; each of the foregoing being incorporated by reference).

An effective amount of the cells is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Bone Marrow Cell Preparation and Culture. Human bone marrow samples were obtained from normal volunteers following informed consent. Bone marrow cells were subjected to plastic adherent cell depletion. Briefly, whole bone marrow is diluted in tissue culture media and layered onto a density gradient, centrifuged, and low-density cells (LD) isolated by density centrifugation collected (density gradient centrifugation may be performed on Histopaque-1077 (1.077 g/mL; Sigma, St. Louis, Mo.) and non-adherent low-density cells prepared as described by Long et al., 1988). LD cells are subjected to plastic-adhesion for 2–18 h (times>two h are immaterial to process, routine is 18 hrs/overnight), and the non-adherent (NA) cells collected. Briefly, cells were collected from the interface and washed three times in Iscove's modified Dulbecco's medium (IMDM; Gibco, Grand Island, N.Y.). The resulting low density cells were counted and subjected to two rounds of plastic adherence at $4 \times 10^5$ cells/cm$^2$ in McCoys 5A media containing with 10% FCS. After the two rounds of plastic adherence, each lasting at least one h at 37° C., low density plastic non-adherent (NALD) cells were collected and washed once in column buffer (PBS/0.5% BSA/0.1% glucose).

The resultant NALD cells are labeled with a cocktail of antibodies to osteonectin (e.g., 10 μg of mouse anti-bovine ON) and osteocalcin (e.g., 10 μg of mouse anti-bovine OC). Antigen-positive cells are labelled with paramagnetic particles conjugated to goat anti-mouse IgG secondary antibody (Miltenyi, Auburn, CA). Labeled cells are exposed to an isolation column in a magnetic field that retains human bone precursor cells, and allows the remainder of the NALD cells to elute. This eluted fraction forms the starting fraction for isolation of the bone marrow derived accessory cells (effector cells). The cells remaining in the magnetic field are human bone precursor cells (target cells). At 200 to 1 E:T ratios bone marrow derived accessory cells at this level of separation produce a soluble growth factor (Osteogenic Stimulatory Activity) that stimulates a 13-fold ex vivo expansion of human bone precursor cells. Bone cells were cultured in supplemented McCoy's 5A media (Long el al, 1988) containing 1% ITS+(Collaborative Research, Bedford, Mass.) as described previously (Long et al., 1990).

Isolation of Bone Marrow Derived Accessory Cells. Cells expressing TGFβ receptor were isolated using a procedure described previously (Long et al., 1992). Bone marrow derived accessory cells were separated by immune adherence to tissue culture dishes coated with antibody to type II TGFβ receptor (TGFβRII). The antibody (Santa Cruz Biotechnology, Santa Cruz, Calif.) at 10 μg/mL in PBS was immobilized by adsorption onto tissue culture plastic for 12–18 h at 37° C. The antibody solution was removed, plates were washed three times with PBS, and non specific binding sites were blocked by incubation of the plates with 1% BSA solution for one hour. Approximately 2.5–6.5×10$^5$ NALD cells per cm$^2$ were incubated on antibody-coated dishes for one h at 37° C. Subsequently, non-adherent cells were removed with three rounds of gentle washing using serum-free McCoy's media containing 1% BSA. Immune adherent cells were removed by gentle scraping with a plastic cell scraper and collected in column buffer with the addition of 100U/mL Dnase.

TGFβ RII-positive cells retain all the Osteogenic Stimulator Activity. Negative cells are inactive. TGFβ RII-positive cells are further purified by fluorescence-activated flow cytometry (FACS) using a Coulter Elite ESP cell sorter and analyzed using Coulter Elite software (Coulter, Miami, Fla.). OACs were collected on the basis of forward light scatter (FSC) and 90-degree light scatter (SSC). Cells with low or high SSC characteristics were sorted and collected into serum free media as described below. This $SSC^{lo}$ TFG-β RII-positive subpopulation retains all the osteogenic stimulatory activity. Cells were then pooled and pelleted, counted, and used for further analysis or culture. For isolation of subpopulations of the OACs, TGFβ RII$^+$ cells were labeled with appropriate FITC-conjugated antibody prior to sorting as described above. With an acquisition gate set on the $SSC^{lo}$ cell population, cells were sorted on the basis of FITC fluorescence at the 530 nM wavelength.

Antibodies, Immune-Adherence, and Immunochemistry. The expression of bone protein antigens was determined by fluorescence activated flow cytometry, or by immunocytochemistry utilizing a avidin-biotin system as previously described (Long et al., 1990; Long and Heffner, 1988). These antibodies are specific for their respective antigens and do not cross-react with other matrix proteins (Stenner et al., 1984; Shull et al., 1989). The monoclonal antibody to bone alkaline phosphatase (SAOS2-P80) was raised to osteosarcoma cells as described elsewhere (Shull et al., 1989). This antibody was proven to detect alkaline phosphatase activity by immunoprecipitation, and by direct protein sequence-analysis of the precipitated antigen.

Flow Cytometric Analysis. Flow cytometric analysis was performed using a Becton-Dickinson FACSCAN system and data analyzed with the BD Lysis software program (Long et al., 1992). Controls consisted of autofluorescence as well as non-specific fluorescence detected with isotype-specific murine monoclonal antibody to keyhole lympet hemocyanin (KLH) from Becton Dickinson. In order to visualize the osteonectin antigenic determinant in two-antigen (two-color) cytometric analysis, the magnetically isolated cells are then incubated for 15 min at 4° C. with strept-avidin conjugated to PerCP (Becton Dickinson). Immunomagnetically purified cells were analyzed for fluorescence intensity versus size (laser-light forward angle scatter), as well as intracellular complexity (laser-light side scatter).

RT-PCR Assay: Total cellular RNA was recovered by lysing the cells directly in Stat-60 according to the directions of the manufacturer (Tel-Test Inc., Friendswood, Tex.). RNA integrity and purity was checked by electrophoresis with ethidium bromide and absorbance at A260/A280. RNA (1.0 mg), 10X RT buffer (1X RT buffer: 50 mM Tris HCl, pH. 8.3, 50 mM KCl, 8.0 mM $MgCl_2$, and 10 mM dithiothreitol), 25 mM dXTP mix (25 mM of each dXTP (ACGT)), 3.0 mg oligo d(T), and 2.5 U reverse transcriptase (M-MLV Reverse Transcriptase, GIBCO-BRL) were incubated together at 38° C. for one hour. One-fifth of the double-stranded product was mixed with 10X Taq buffer (1X Tag/RT buffer: 10 mM Tris (pH 8.3), 50 mM KCI, 1.5 mM $MgCl_2$, 0.01% gelatin, and 2.0 mmol/L dithiothreitol), 1 mM dXTP mix, 500 ng of each sense and antisense oligonucleotides, and 2.5 U Taq polymerase (Taq polymerase GIBCO-BRL). Sense and antisense primers were prepared by the oligonucleotide synthesis core at the University of Michigan and were designed to cross intron/exon boundaries (See Sequence Listing). The samples underwent thermal cycling at 94° C. for 1 min and 72° C. for 3 minutes for 35 cycles, followed by a 10 min extension at 72° C. (Perkin Elmer Cetus DNA thermal cycler). The products were electrophoresed in 3% agarose and visualized using ethidium bromide. To control for false positives due to "overamplification" or genomic DNA contamination, reverse transcriptase was omitted from the reaction and primers were designed to cross intron/exon boundaries. Where indicated, positive RNA specimens were included in the analyses. These included IL-1α and TNF-α stimulated human bone marrow stroma, peripheral blood lymphocytes stimulated with PHA (3.0 μg/ml) and PMA (3 ng/ml) for 18 h or RNA from human bone osteosarcoma cell lines MG-63 or SaOS-2.

Cell Culture: When necessary, cells grown in a bone precursor cell/OAC co-culture were physically separated by embedding the OAC feeder layer in a 0.5% semi-solid agar layer that allows the free diffusion of soluble growth factors, while preventing cell:cell contact between the target cells and feeder cells. Appropriate cells numbers of OACs were suspended in serum-free McCoy's medium (Gibco-BRL, Grand Island, N.Y.) supplemented with ITS$^+$ and 100 pM TGFβ (Collaborative Biomedical Products, Bedford, Mass.). Cell suspension was warmed to 37° C. before 0.1 volume of molten 5% agar (in PBS) was added, mixed, and pipetted into a culture dish before being allowed to cool briefly. Next, (target) human bone precursor cells suspended in McCoys mediuni/ITS/TGFβ were layered onto the agar layer, and cultured seven days at 37° C.

EXAMPLE 2

Human Bone Accessory Cells Regulate Bone Precursor Cell Proliferation and Survival Highly purified HBPC, in the presence of TGFβ, fail to survive or proliferate over seven days of culture (FIG. 1A). Bone marrow derived accessory cells that have been isolated according to the methods described herein, reconstitute survival, prolifeiation and bone protein expression when admixed with HBPC. The inmmunocytochemical expression of osteocalcin is shown in FIG. 1A and FIG. 1B. In addition, it was found that the HBPC that have been reconstituted with the bone marrow accessory cells also express other bone proteins such as osteonectin and alkaline phosphatase.

In order to determine whether the bone-cell reconstitution was mediated by a soluble factor or cell:cell contact, bone marrow derived accessory cells were established as feeder layers of 0.5% agar in which cell:cell contact cannot occur. Feeder layers of bone marrow derived accessory cells (i.e., effector cells) stimulate up to a 13±2—fold ex vivo expansion of HBPC (Target cells), at E to T ratios of 100 to 200: 1, (FIG. 2, columns 4–6) indicating that the accessory cell effect is mediated by a soluble growth factor. Culture of bone cells in the absence or presence of TGFβ (cols. 1 and 2) fails to support their development, and culture of these cells alone does not evidence osteogenic potential (column 3).

Figure 3A:
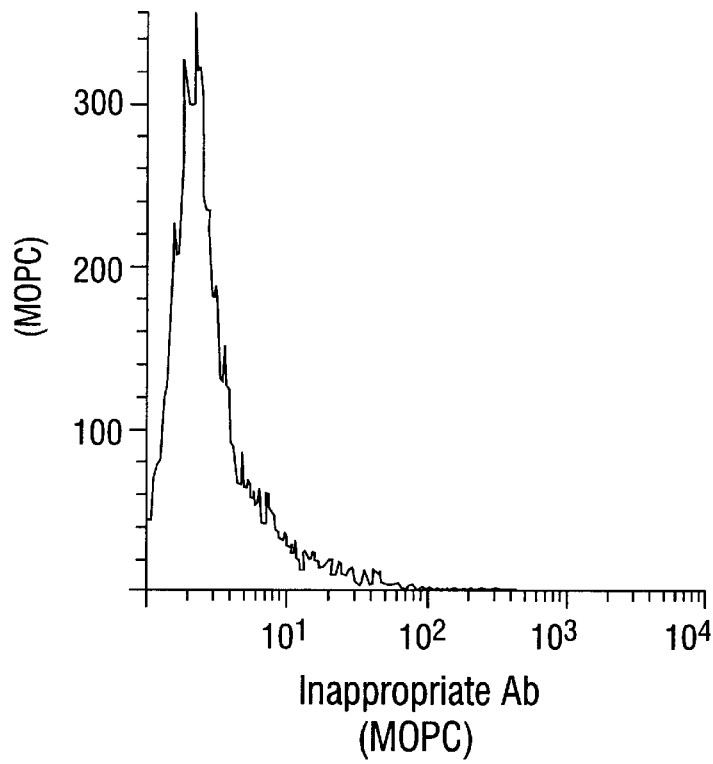
FIG. 3A, FIG. 3B, FIG. 3C and FIG. 3D. Typical Bone Marrow Accessory Cells Are Not Found Among Known Bone Marrow Accessory Cell Populations. Isolated populations of bone marrow derived accessory cells were evaluated for expression of antigenic markers of typical bone marrow-derived accessory cell populations of T-cells (CD3.
Figure 3B:
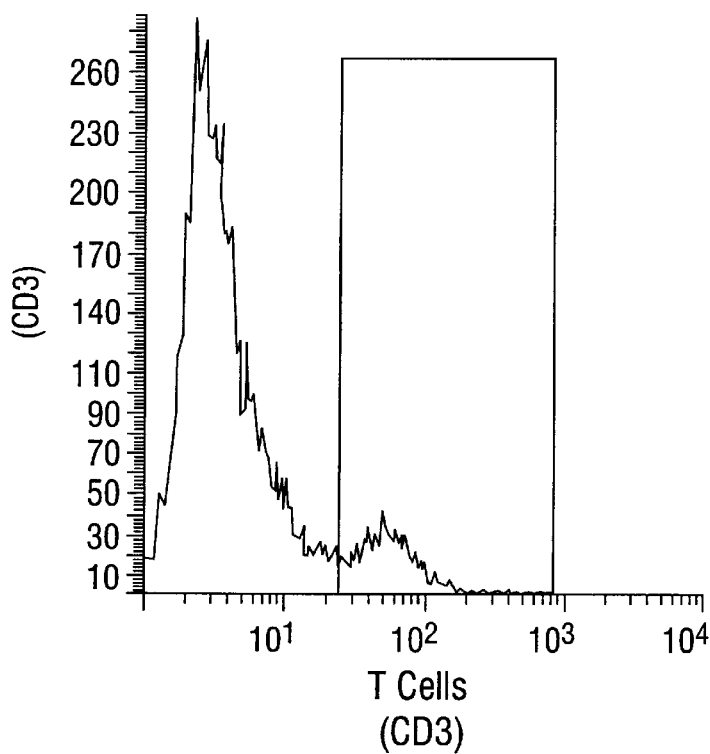
Figure 3C:
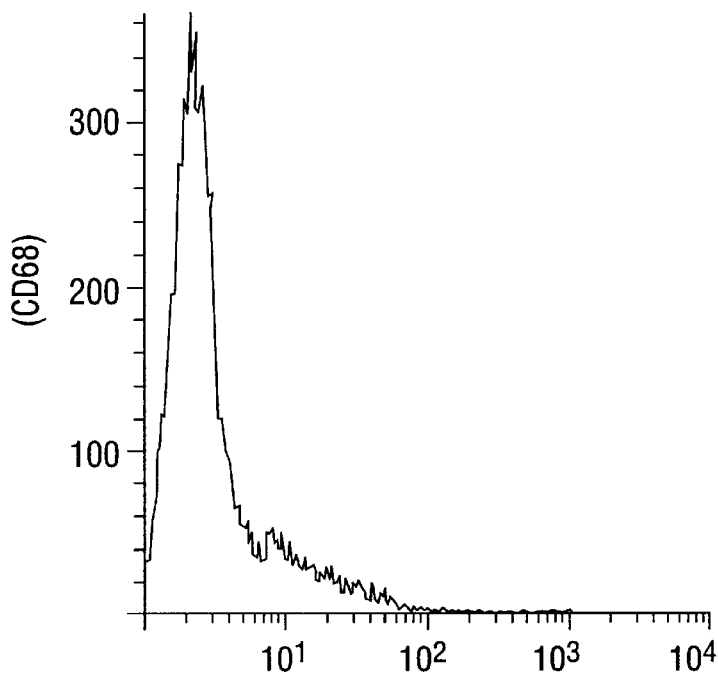
Figure 3D:
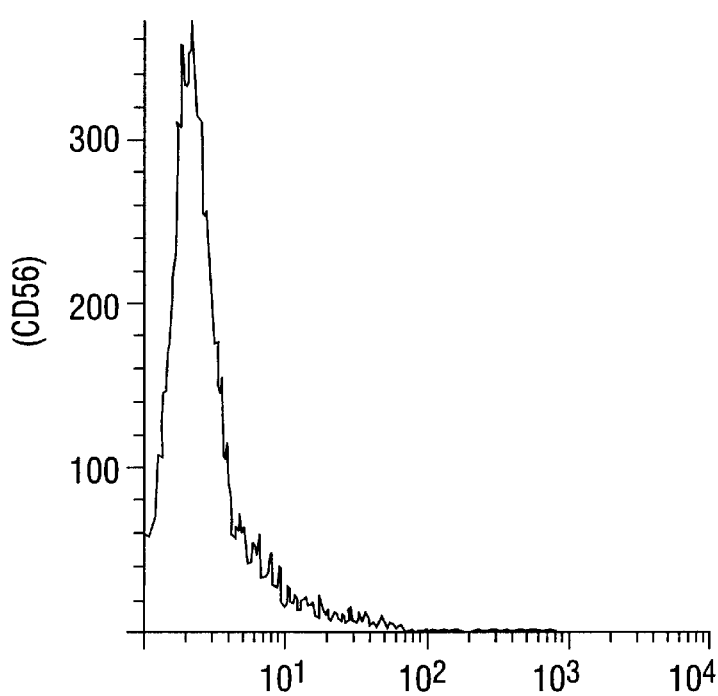

Isolated populations of bone marrow derived accessory cells were evaluated for expression of antigenic markers of T-cells (CD3; FIG. 3B), macrophages (CD65; FIG. 3C), and NK cells (CD56; FIG. 3D). Only a subpopulation of T-cells (FIG. 3B, boxed population) is observed. However, these cells do not persist>24–48 h in culture, and their (prior) removal does not eliminate bone marrow derived accessory cell activity. These data show that typical bone marrow stromal/accessory cells fail to support human bone precursor cells.

Figure 4:
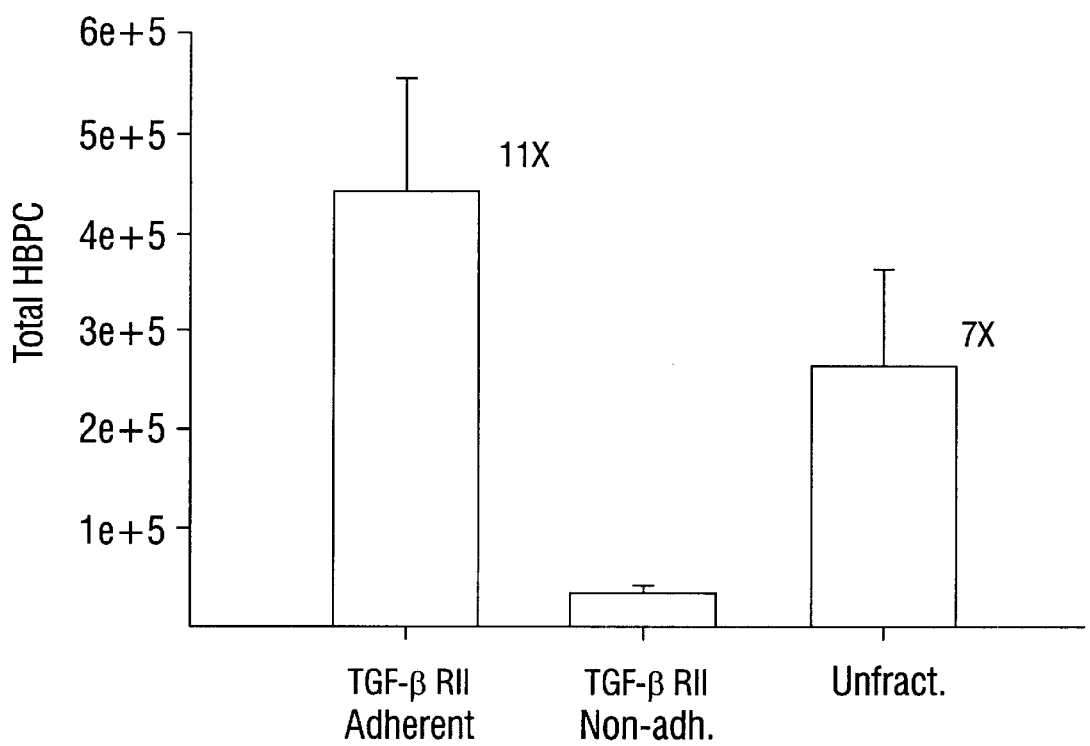
FIG. 4. TGFβ Receptor, Type II (TGFβRII)—Positive Cells Express an Osteopoietic Stimulatory Activity (OSA). TGFβRII⁺ accessory, or "osteogenic," cells were isolated by immune adherence and established as feeder layers to support HBPC. The receptor-positive subpopulation retains OSA whereas the receptor-negative population fails to stimulate the HBPC target cells, thus showing that bone accessory cells express TGFβII. adh.=adherent.
Figure 5A:
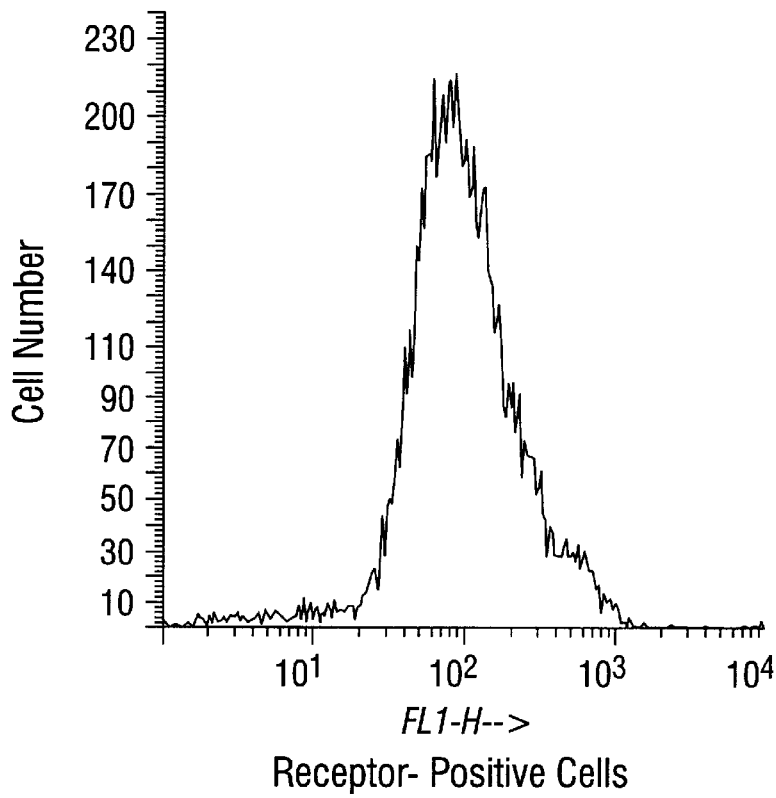
FIG. 5A and FIG. 5B. Subpopulations of Accessory Cells Express High Levels of TGFβRII Cells and are Distinguished by their Internal Complexity (Side Scatter Characteristics; SSC). Flow cytometric evaluation of TGFβRII⁺-expressing bone accessory cells indicate that two populations are present that are distinguished by their internal complexity, as indicated by the degree of 90° (side) scatter of the laser beam.
Figure 5B:
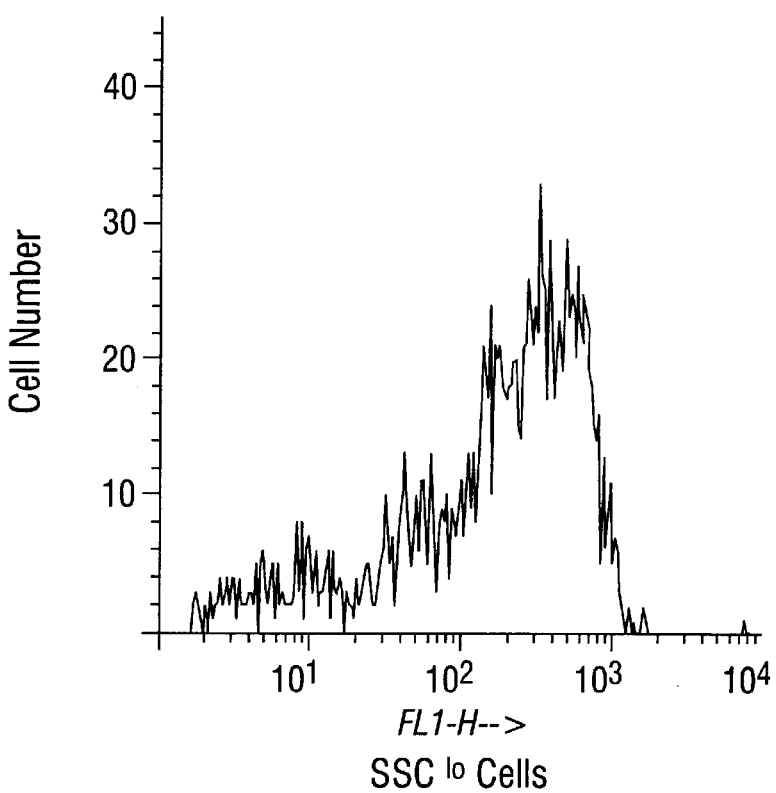

The obligate requirement for TGFβ stimulation suggested that the accessory cells should express the receptor for this growth factor. TGFβRII⁺ cells were isolated by immune adherence and established as feeder layers to support HBPC. It was shown that TGFβRII positive cells express an osteogenic stimulatory activity (OSA) (FIG. 4). Thus, the receptor-positive subpopulation retains OSA whereas the receptor-negative population fails to stimulate the HBPC target cells.

In a further characterization of the low density, non-adherent, TGFβRII-positive cells that possess OSA, it was found that the subpopulations of TGFβRII-positive cells could be distinguished by their internal complexity, according to their side light scatter characteristics during flow cytometry. Flow cytometric evaluation of TGFβRII-expressing bone marrow derived accessory cells indicate that subpopulations are present that are distinguished by their internal complexity, as shown by the degree of 90° (side) scatter of the incident laser beam. To accomplish this, cells were isolated by immune adherence using TGFβRII antibodies. Examination of the isolated cells shows a high expression of TGFβRII (left panel) compared to inappropriate antibody staining. Analysis of the flow cytometry data revealed two populations of TGFβRII⁺ cells distinguished by their side scatter characteristic (SSC). Among these the SSC-low subpopulation (right panel) expressed high amounts of TGFβRII (FIG. 5A–FIG. 5B and FIG. 6A–FIG. 6C).

Figure 7:
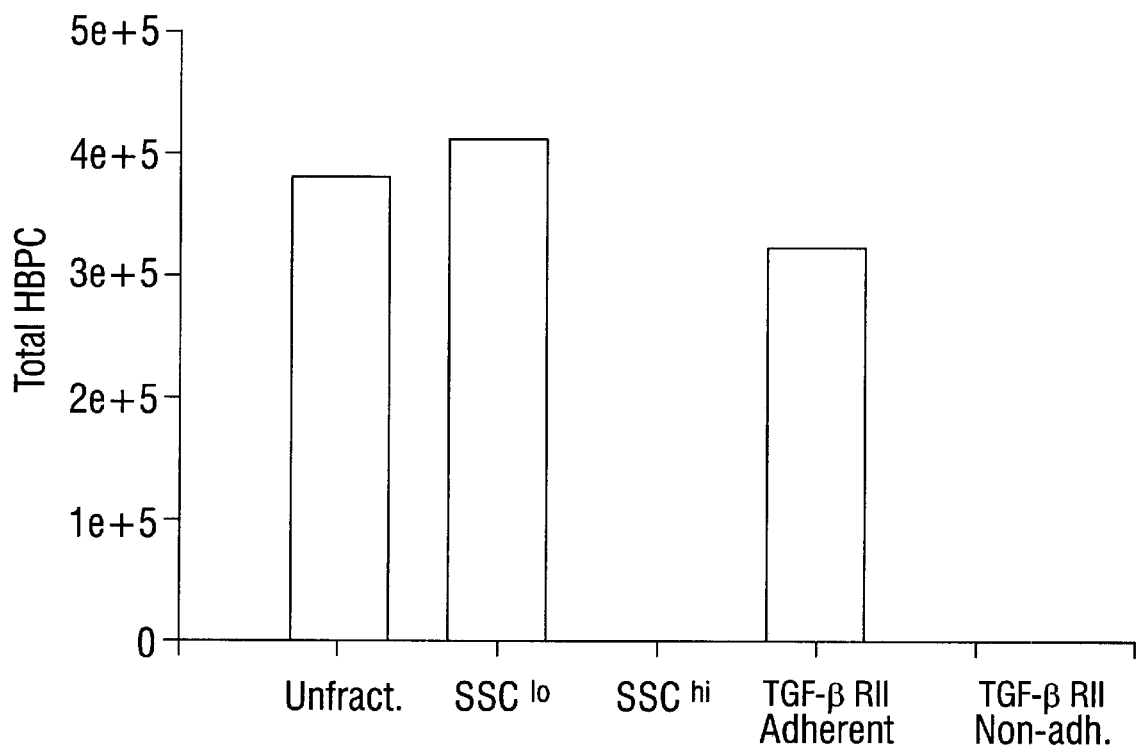
FIG. 7. Osteogenic Stimulatory Activty Co-Segregates With Subpopulations of TGFβRII-Positive, $SSC^{lo}$ Cells. Purified populations (as defined in FIG. 6) were established as feeder layers to stimulate HBPC. All OSA is retained in the $SSC^{lo}$ and TGFβRII⁺ populationa, whereas the $SSC^{hi}$ and TGFβII cells fail to support the HBPC Target cells. These data define the accessory cell populations as TGFβII⁺ and $SSC^{lo}$. Unfractionated bone marrow derived accessory cells=Ufract.

The distinguishing side-scatter characteristic discussed above allows the separation of TGFβRII⁺ cells by fluorescence-activated cell sorting into the purified subpopulations of TGFβRII⁺/SSC$^{hi}$ cells and TGFβRII⁺/SSC$^{lo}$ cells (≧92% pure). In order to understand the significance of the two SSC subpopulations found within the TGFβRII⁺ cells, these sorted cells were established as OAC-feeder layers for human bone precursor cells. When established as feeder layers in TGFβ-containing media, unfractionated or TGFβRII⁺ cells both support an 8-fold ex vivo expansion of human bone precursor cells over seven days of culture. During this time, the target cells maintained the phenotype of human bone precursor cells. Moreover, TGFβRII-negative cells lacked OAC activity, as did the TGFβRII$^{hi}$/SSC$^{hi}$ cells. In sharp contrast, isolation of TGFβRII$^{hi}$/SSC$^{lo}$ cells results in an 8-fold increase (8.0±1.4, mean ±SEM n=3) in their OAC specific activity. These studies demonstrate that the OSA was retained in the SSC$^{lo}$ population, whereas the SSC$^{hi}$ cells failed to support the HBPC target cells. The purification of TGFβ-RII⁺/SSC$^{lo}$ cells results in an approximate 8-fold increase in OAC activity (on a per cell basis), with a resulting population of cells that are very homogeneous. Given their appearance as small, lymphoid appearing cells, they were evaluated for T-cell (see above) and B-cell markers. A sub-population (approximately 10%) of the TGFβ-RII⁺/SSC$^{lo}$ cells expressed the B-cell antigens CD10 and CD19. However, sorting studies of this population indicated that the CD10⁺/CD19⁺ cells lacked OAC activity. Likewise, the TGFβRII positive, non-adherent cells did not possess OSA (FIG. 7). Thus, the accessory cells are TGFβRII-positive, SSC$^{lo}$. Thus, all of the OAC population exists within a TGFβ-RII⁺/SSC$^{lo}$ population of cells that can be isolated by fluorescence-activated cell sorting.

Figure 8:
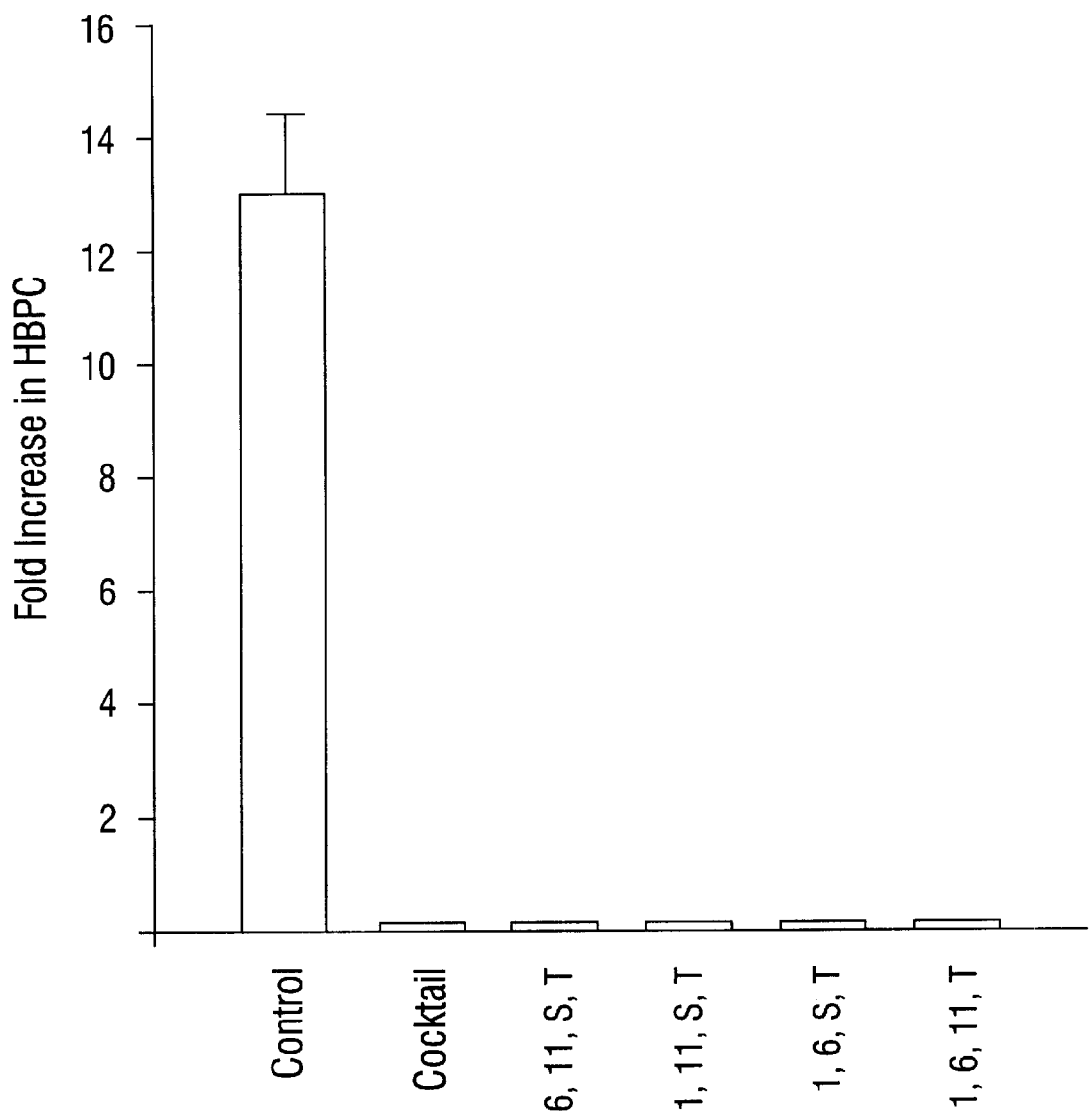
FIG. 8. Cytokines Expressed by Bone Marrow Derived Accessory Fail to Support HBPC Development. Based on RT-PCR™ analysis, combinations of cytokines expressed by TGFβ-stimulated bone marrow derived accessory cells were used to stimulate HBPC. None of these combinations, nor solitary factors were able to substitute for bone marrow derived accessory cells (Control). IL=Interleukin; 1=IL-1; 6=IL-6; 11=IL-11; S=SCF, T=TGFβ; cocktail=combination of 1, 6, 11, S and T.

Based on RT-PCR™ analysis, combinations of cytokines expressed by TGFβ-stimulated bone marrow derived accessory cells were used to stimulate HBPC. The constitutively expressed cytokines include TGFβ1, SCF, Flk 2-lig., IL-1α. None of these cytokines in combination, nor as a solitary factor, were able to substitute for accessory cells (Control; FIG. 8), thereby demonstrating that the accessory cells contain a factor with osteogenic stimulatory activity that is distinct from these known cytokines and factors. The bone marrow accessory cells do not appear to express BMP-2, BMP-4, LIF, IL-11 or βFGF.

According to previous reports, several growth factors (some of which are constitutively-expressed by OAC), including IL-1α, IL-6 and IL-11, are implicated in osteoblast development (Bellido et al., 1996; Dodds et al., 1994). Based on these reports and the OAC cytokine expression profile, cocktails of candidate growth factors were utilized in an attempt to replace the osteopoietic stimulatory effect of the accessory cells. Cocktails containing IL-1, 6, 11, SCF, and TGFβ, alone or in various combinations, failed to replace the accessory cell population, suggesting that OAC cells elaborate a unique growth factor(s) that stimulates the early phase of bone cell development (osteopoiesis). As well, the cytokines VEGF and EGF do not replace the OAC in the reconstruction of bone cell phenotype (not shown).

In conclusion, the inventors have isolated a bone accessory cell population of low cellular complexity, and high amounts of TGFβRII. This accessory cell population is capable of reconstituting both the proliferation and bone protein expression of highly purified HBPC. Furthermore, this cell population produces an OSA that cannot be replaced by known cytokines or a variety of exogenous growth factors.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically or physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Antibodies "A LABORATORY MANUAL, E. Harlow and D. Lane, Cold Spring Harbor Laboratory, 1988.

Aizawa, et al, "Establishment of a variety of human bone marrow stromal cell lines by the recombinant SV40-adenovirus vector," *J. Cell. Physiol*, 148:245–251, 1991.

Allen and Dexter, "The essential cells of the hemopoietic microenvironment," *Exp. Hematol.*, 12:517, 1984.

Altman et al., *Diabetes* 35:625–633, 1986.

Antibodies: A Laboratory Manual, Cold Spring Harbor Laboratory, Cold Spring Harbor Press, Cold Spring Harbor, N.Y., 1988.

Ash el al., "Osteoclasts derived from haematopoietic stem cells," *Nature*, 283:669–670, 1980.

Bellido et al., "Detection of receptors for interleukin-6, interleukin-11, leukemia inhibitory factor, oncostatin M, and ciliary neurotropic factor in bone marrow stromal/osteoblastic cells." *J Clin. Invest*. 97:431–437, 1996.

Campbell et al., "Developmental regulation of granulocytic cell binding to hemonectin," *Blood*, 76:1758–1764, 1990.

Campbell et al., "Extracellular matrix promotes-the growth and differentiation of murine hematopoietic cells in vitro," *J Clin. Invest.*, 75:2085–2090, 1985.

Campbell et al., "Haemonectin, a bone marrow adhesion protein specific for cells of granulocyte lineage," *Nature*, 329:744–746, 1987.

Canalis, "Effect of growth factors on bone cell replication and differentiation," *Clin. Orth. ReL Res.*, 193:246–263, 1985.

Ciuttini el al., "Support of human cord blood progenitor cells on human stromal cell lines transformed by SV40 large T-antigen under the influence of an inducible (metallothionein) promoter," *Blood*, 80:102–112, 1992.

Coccia et al., "Successful bone-marrow transplantation for juvenile malignant osteopetrosis," *N. Engl. J. Med.*, 302:701–708, 1980.

Collins and Dorshkind, "A stromal cell line from myeloid long-term bone marrow cultures can support myelopoiesis and lymphopoiesis," *J. Immunol*, 138:1082, 1987.

Dexter et al., "Stromal cell associated haemopoiesis," *J. Cell Physiol.*, 1:87, 1982.

Dexter et al., Conditions controlling the proliferation of haemopoietic stem cells in vitro, *J. Cell. Physiol.*, 91:335, 1977.

Dodds et al., "Expression of mRNA for IL1α, IL6 and TGFβ1 in developing human bone and cartilage." *J. Histochem. Cytochem.* 42:733–744, 1994.

Fibbe et al., "Interleukin- 1 induced human marrow stromal cells in long-term marrow culture to produce granulocyte colony-stimulating factor and macrophage colony-stimulating factor," *Blood*, 71:430, 1988.

Fields et al., In: *Virology*, 2nd ed., Raven Press, New York, USA, pp. 1593–1607, 1990.

Fishman and Hay, "Origin of osteoclasts from mononuclear leukocytes in regenerating newt limbs," *Anat. Rec.*, 143:329–339, 1962.

Freifelder, In: *Physical Biochemistry Applications to Biochemistry and Molecular Biology*, 2nd ed., Wm. Freeman and Co., New York, N.Y., 1982.

Fritschy et al., *Diabetes*, 40:37, 1991.

Gartner and Kaplan, "Long-term culture of human bone marrow cells," *Proc. Nat'l. Acad Sci. USA*, 77:4756, 1980.

Gehron Robey et al., "Osteoblasts synthesize and respond to transforming growth factor-type beta (TGF-beta) in vitro," *J. Cell Biol.*, 105:457–463, 1987.

Gospodarowicz and Ill, "Extracellular matrix and control of proliferation of vascular endothelial cells," *J. Clin. Invest.*, 65:1351–1364, 1980.

Gospodarowicz et al., "Permissive effect of the extracellular matrix on cell proliferation in vitro," *Proc. Nat'l Acad Sci. USA*, 77:4094–4098, 1980.

Gronthos et al., "The STRO-1⁺ fraction of adult human bone marrow contains the osteogenic precursors." *Blood* 84:4164–4173, 1994.

Gualtieri et al., "Hematopoietic regulatory factors produced in long-term murine bone marrow cultures and the effect of in vitro irradiation," *Blood*, 64(2):516–525, 1984.

Hanamura et al., "Solubilization and purification of bone morphogenetic protein (BMP) from dunn osteosarcoma," *Clin. Orth. Rel. Res.*, 153:232–240, 1980.

Harigaya and Handa, "Generation of functional clonal cell lines from human bone marrow stroma," *Proc. Nat'l Acad Sci. USA*, 82:3477, 1985.

Harigaya et al., "Generation of functional clonal cell lines from human bone marrow stroma," *Proc. Nat'l Acad Sci. USA*, 82:3477–3480, 1985.

Hattersley and Chambers, "Generation of osteoclastic function in mouse bone marrow cultures: multicellularity and tartarate resistant acid phosphatase are unreliable markers of osteoclastic differentiation," *Endocrinology*, 124:1689–1696, 1989.

Hauschka et al., "Growth factors in bone matrix. Isolation of multiple types by affinity chromatography on heparin-sepharose," *J. Biol. Chem.*, 261:12665–12674, 1986.

Hocking and Golde, "Long-term human bone marrow cultures," *Blood*, 56:117, 1980.

Holland et al., "In vivo expression of mRNA for the Ca++-binding protein SPARC (osteonectin) revealed by in situ hybridization," *J. Cell Biol.*, 105:473–482, 1987.

Horton et al., "Monoclonal antibodies to osteoblastomas (giant cell bone tumors): definition of osteoclastic specific cellular antigens," *Cancer Res.*, 45:5663–5669, 1985.

Hunt et al., "A single bone marrow-derived stromal cell type supports the in vitro growth of early lymphoid and myeloid cells," *Cell*, 48:997, 1987.

Ignotz and Massague, "Transforming growth factor-beta stimulates the expression of fibronectin and collagen and their incorporation into the extracellular matrix," *J. Biol. Chem.*, 261:4337–4345M, 1986.

Jotereau and Le Douarin, "The developmental relationship between osteocytes and osteoblasts: A study using the quail-chick nucleus marker in endochondrial ossification," *Dev. Biol.*, 63:253–265, 1978.

Kaushansky et al., "Interleukin 1 stimulates fibroblasts to synthesize granulocyte-macrophage and granulocyte colony-stimulating factors," *J. Clin Invest*, 81:92, 1988.

Kohama et al., "A burst-promoting activity derived from the human bone marrow stromal cell line KM-102 is identical to the granulocyte-macrophage colony-stimulating factor," *Exp. Hematol.*, 16:603–608, 1988.

Lacy et al., *Science*, 254:1782–1784, 1991.

Lanotte et al., "Histochemical and ultrastructural characteristics of a cell line from human bone marrow stroma," *J. Cell. Sci*, 50:281, 1981.

Le Douarin, C R, Acad *Sci. Heb'd Seances. Acad Sci. D.* 22;276(4):629–32, 1973 Lee et al., "Interleukin 1 induces human bone marrow-derived fibroblasts to produce multilineage hematopoietic growth factors," *Exp. Hematol.*, 15:983, 1987.

Linkhart et al., "Characterization of mitogenic activities extracted from bovine bone matrix," *Bone*, 7:479–487, 1986.

Long and Dixit, "Thrombospondin functions as a cytoadhesion molecule for human hematopoietic progenitor cells," *Blood*, 75:2311–2318, 1990.

Long and Heffner, "Detection of human megakaryocyte antigens by solid-phase radioimmunoassay," *Exp. Hematol.*, 16:62–70, 1988.

Long et al., "Cholera toxin and phorbol diesters synergistically modulate murine hematopoietic progenitor cell proliferation," *Exp. Hematol.*, 16:195–200, 1988.

Long et al., "Expression of bone-related proteins in the human hematopoietic microenvironment," *J. Clin. Invest.*, 86:1387–1395, 1990.

Long et al., "Human hematopoietic stem cell adherence to cytokines and matrix molecules," *J. Clin. Invest.*, 90:251–255, 1992.

Long et al., "Regulation of megakaryocyte potential in human erythroleukemia cells," *J. Clin. Invest.*, 85:1072–1084, 1990.

Long et al., "Synergistic regulation of human megakaryocyte development," *J. Clin. Invest.*, 82:1779–1786, 1988.

Long et al., "Human Bone marrow contains a population of cells capible of producing bone proteins." *Blood* 72:95a (Abstr.) 1989.

Long el al., "Regulation of human bone marrow-derived osteoprogenitor cells by osteogenic growth factors." *J. Clin. Invest* 95:881–887, 1995.

Long, "Blood cell cytoadhesion molecules," *Exp. Hematol.*, 20:288–301, 1992.

Massague, "The TGF-beta family of growth and differentiation factors," *Cell*, 49:437–438, 1987.

Morgan, B. P., Complement—Clinical Aspects and Relevance to Disease (Academic Press, London), 1990.

Muthukumaran and Reddi, "Bone matrix-induced local bone induction," *Clin. Orth. Rel. Res.*, 200:159–164, 1985.

Nemunaitis et al., "Human marrow stromal cells: Response to interleukin-6 (IL-6) and control of IL-6 expression," *Blood*, 74:1929–1935, 1989.

Nemunaitis et al, "Response of simian virus 40 (SV40)-transformed, cultured human marrow stromal cells to hematopoietic growth factors," *J. Clin. Invest.*, 83:593–601, 1989.

Neufeld et al., "Immortalization of human fibroblasts transformed by origin-defective simian virus 40," *Molecular Biology*, 7(8):2794–2802, 1987.

Nomura et al., "Developmental expression of 2ar (osteopontin) and SPARC (osteonectin) RNA as revealed by in situ hybridization," *J. Cell Biol.*, 106:441–450, 1988.

Novotny et al., "Cloned stromal cell lines derived from human Whitlock/Wittetype long-term bone marrow cultures," *Exp. Hematol.*, 18:775, 1990.

O'Shea and Sun, *Diabetes*, 35:943–946, 1986.

Oldberg et al., "Cloning and sequence analysis of rat bone sialoprotein (osteopontin) cDNA reveals an Arg-Gly-Asp cell-binding sequence," *Proc. Nat'l Acad Sci. USA*, 83:8819–8823, 1986.

Price et al., "Characterization of a gamma-carboxyglutamic acid-containing protein from bone," *Proc. Nat'l Acad Sci. USA*, 73:1447–1451, 1976.

Price et al., "Developmental appearance of the vitamin K-dependent protein of bone during calcification. Analysis of mineralizing tissues in human, calf, and rat," *J. Biol. Chem.*, 256:3781–3784, 1981.

Quesenberry et al., "Multilineage synergistic activity produced by a murine adherent marrow cell line," *Blood*, 69:827, 1987.

Reddi, "Cell biology and biochemistry of endochondral bone development," *Coll. Res.*, 1:209–226, 1981.

Reh and Gretton, "Retinal pigmented epithelial cells induced to transdifferentiate to neurons by laminin," *Nature*, 330:68–71, 1987.

Reid, K. B. M., Complement (IRL Press, Oxford), 1988.

Rickard et al., "Isolation and characterization of osteoblast precursor cells from human bone marrow." *J. Bone Miner. Res.* 11:312–324. 1996.

Shull et al., "Identification of a vitamin D responsive protein on the surface of human osteosarcoma cells," *Proc. Nat'l Acad. Sci. USA*, 86:5405–5410, 1989.

Simmons and Torok-Storb, "Identification of stromal cell precursors in human bone marrow by a novel monoclonal antibody, STRO-1." *Blood* 78:55–62, 1991.

Singer et al., "Simian Virus 40-transformed adherent cells from human long-term marrow cultures: cloned cell lines produce cells with stromal and hematopoietic characteristics," *Blood*, 70:464–474, 1987.

Slack et al., "Regulation of cytokine and growth factor gene expression in human bone marrow stromal cells transformed with simian virus 40," *Blood*, 75:23 19–2327, 1990.

Somerman et al., "Mechanism of fibroblast attachment to bone extracellular matrix: Role of a 44kilodalton bone phosphoprotein," *J. Bone Min. Res.*, 2:259–265. 1987.

Sporn and Roberts, "Autocrine growth factors and cancer," *Nature*, 313:745–747, 1985.

Stenner et al., "Monoclonal antibodies to native noncollagenous bone-specific proteins," *Proc. Nat'l Acad. Sci. USA*, 81:2868–2872, 1984.

Sullivan et al., *Science* 252:718–721, 1991.

Termine et al., "Osteonectin, a bone-specific protein linking mineral to collagen," *Cell*, 26:99–105, 1981.

Thalmeier et al., "Establishment and characterization of human bone marrow stromal cell lines," *Experimental Hematology*, 20(6):815, 1992.

Thatmeier et al., "Establishment of two permanent human bone marrow stromal cell lines with long-term post irradiation feeder capacity," *Blood*, 83 (7):1799–1807, 1994.

Toksoz et al., "Support of human hematopoiesis in long-term bone marrow cultures by murine stromal cells selectively expressing the membrane-bound and secreted forms of the human homolog of the steel gene product, stem cell factor." *Proc. Nat'l Acad. Sci. USA* 89:7350–7354, 1992.

Toogood et al., The development of a liquid culture system for the growth of human bone marrow., *Leuk. Res.*, 4:449, 1980.

Turksen and Aubin, "Positive and negative immunoselection for enrichment of two classes of osteoprogenitor cells." *J. Cell Biochem.* 1 14:373–384, 1991.

U.S. Pat. No. 4,916,265
U.S. Pat. No. 5,199,942
U.S. Pat. No. 5,409,825
U.S. Pat. No. 5,486,359
U.S. Pat. No. 5,599,703
U.S. Pat. No. 5,605,822
U.S. Pat. No. 5,646,043
U.S. Pat. No. 5,658,761
U.S. Pat. No. 4,892,538
U.S. Pat. No. 5,002,661
U.S. Pat. No. 5,011,472
U.S. Pat. No. 5,314,471
U.S. Pat. No. 5,545,223
U.S. Pat. No. 5,549,675
U.S. Pat. No. 5,569,462
U.S. Pat. No. 5,593,440
U.S. Pat. No. 5,626,561

Urist et al., "Bone cell differentiation and growth factors," *Science*, 220:680–686, 1983.

Urist et al., "Human bone morphogenic protein (hBMP)," *Proc. Soc. Exp. Biol. Med.*, 173:194–199, 1983.

Wicha et al., "Extracellular matrix promotes mammary epithelial growth and differentiation in vitro," *Proc. Nat'l Acad. Sci. USA*, 79:3213–3217, 1982.

Williams et al., "Generation of murine stromal cell lines supporting hematopoietic stem cell proliferation by use of recombinant retrovirus vectors encoding SV40 large T antigen," File Server STN Karlsruhe, File Biosis, Abstract No. 88:460575, *Mol. Cell. Biol.*, 8(9):3864–3871, 1988.

Wilson and Goulding, A Biologist's Guide to Principles and Techniques of Practical Biochemistry, 3rd. Ed., 1986.

WO 89/01967
WO 90/02580
WO 90/15637
WO 91/10425
WO 91/10470

Wozney et al., "Novel regulators of bone formation: molecular clones and activities," *Science*, 242:1528–1534. 1988.

Yang et al., "Interleukin-1 regulation of hematopoietic growth factor production by human stromal fibroblasts," *J. Cell. Physiol*, 134:292–296, 1988.

What is claimed is:

1. A method for isolating a bone osteogenic accessory cell comprising the of:
   (a) prociding a starting cell population;
   (b) subjecting said population to density isolation by equilibrium density centrifugation to obtain a low density cell fraction wherein the low density is about between 1.050 gm/cm$^3$ and about 1.090 gm/cm$^3$;
   (c) subjecting said low density cell fraction to immune adherence isolation based on TDFβII receptor expression and recovering an immune adherent cell; and
   (d) subjecting the immune adherent cell of step (c) to isolation based on low cellular complexity determined by flow cytometric analysis,
   whereby a low complexity cell isolated in step (d) is a vone osteogenic accessory cell.

2. The method of claim 1, further comprising subjecting a cell population or fraction of steps (a)–(c) to plastic adherence, wherein adherent cells are discarded.

3. The method of claim 1, further comprising subjecting said low density cell fraction to an additional immunoaffinity purification.

4. The method of claim 3, wherein said immunoaffinity purification comprises contacting said low density cells with anti-osteonectin antibodies or anti-osteocalcin antibodies or both.

5. The method of claim 4, wherein said immunoaffinity purification comprises contacting said anti-osteonectin or anti-osteocalcin antibodies with an anti-immunoglobulin antibody conjugated to a paramagnetic particle and purifying said paramagnetic particle using a magnetic field.

6. The method of claim 1, wherein step (d) comprises cell sorting.

7. The method of claim 6, wherein said cell sorting comprises fluorescence activated cell sorting (FACS).

8. The method of claim 7, comprising selecting the SSC$^{lo}$ population.

9. The method of claim 1, further comprising subjecting a cell of steps (a)–(d) to negative selection for the expression of P-selectin.

10. The method of claim 1, further comprising subjecting a cell of steps (a)–(d) to negative selection for the expression of L-selectin.

11. The method of claim 1, further comprising subjecting a cell of steps (a)–(d) to negative selection for the expression of E-selectin.

12. The method of claim 1, further comprising subjecting a cell of steps (a)–(d) to negative selection for the expression of CD3.

13. The method of claim 1, further comprising subjecting a cell of steps (a)–(d) to negative selection for the expression of CD56.

14. The method of claim 1, further comprising subjecting a cell of steps (a)–(d) to negative selection for the expression of CD68.

15. The method of claim 1, further comprising subjecting a cell of steps (a)–(d) to negative selection for the expression of CD34.

16. The method of claim 1, further comprising subjecting a cell of steps (a)–(d) to negative selection for the expression of vWF.

17. The method of claim 9, wherein said negative selection comprises FACS.

18. The method of claim 9, wherein said negative selection comprises antibody-mediated complement-dependent cell killing.

19. The method of claim 9, wherein said negative selection comprises immunoaffinity.

20. The method of claim 1, wherein said starting cell population is bone marrow cells or fetal calverial cells.

21. The method of claim 1, further comprising culturing cells of step (a) prior to step (b).

22. The method of claim 1, further comprising culturing cells of step (b) prior to step (c).

23. The method of claim 1, further comprising culturing cells of step (c) prior to step (d).

24. The method of claim 1, further comprising culturing cells of step (d).

25. The method of claim 22, wherein said culturing comprises culturing said cells with an osteogenic cytokine.

26. The method of claim 25, wherein said osteogenic cytokine is a member of the TGFβ super family of cytokines.

27. The method of claim 26, wherein said osteogenic cytokine is TGFβ1 or TGFβ2.

* * * * *

UNITED STATES PATENT AND TRADEMARK OFFICE
CERTIFICATE OF CORRECTION

PATENT NO.     : 6,576,465 B1
DATED          : June 10, 2003
INVENTOR(S)    : Michael W. Long It is certified that error appears in the above-identified patent and that said Letters Patent is hereby corrected as shown below:

Title page,
Item [57], ABSTRACT,
Please delete "Disclosed are compositions of bone accessory cells and methods for their preparation and use. Bone accessory cells are cells which are not hematopoietic and which can reconstitute the expression of bone proteins by human bone cells and support ex vivo expansion and/or differentiation of these cells. Such bone marrow-derived accessory cells are useful in the treatment of bone disorders and diseases, such as osteoporosis, or in promoting fracture repair. In addition, methods of diffenentiating bone precursor cells into osteoblasts, and other diagnostic and prognostic methods are provided." and replace with -- Disclosed are compositions of bone accessory cells and methods for their preparation and use. Bone accessory cells are cells which are not hematopoietic and which can reconstitute the expression of bone proteins by human bone cells and support ex vivo expansion and/or differentiation of these cells. Such bone marrow-derived accessory cells are useful in the treatment of bone disorders and diseases, such as osteoporosis, or in promoting fracture repair. In addition, methods of differentiating bone precursor cells into osteoblasts, and other diagnostic and prognostic methods are provided. -- therefor.

Column 25,
Line 4, delete "prociding" and insert -- providing -- therefor.
Line 10, delete "TDFβII" and insert -- TDF$\beta$II -- thereof.
Line 16, delete "vone" and insert -- bone -- therefor.

Signed and Sealed this

Fourteenth Day of October, 2003

JAMES E. ROGAN
*Director of the United States Patent and Trademark Office*